(12) United States Patent
LaVoie et al.

(10) Patent No.: US 6,399,642 B2
(45) Date of Patent: *Jun. 4, 2002

(54) BENZIMIDAZOLE TOPOISOMERASE POISONS

(75) Inventors: Edmond J. LaVoie, Princeton Junction, NJ (US); Jung Sun Kim, Pusan (KR); Meera Rangarajan, Highland Park; Leroy Fong Liu, Bridgewater, both of NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/796,500

(22) Filed: Feb. 28, 2001

Related U.S. Application Data

(60) Continuation of application No. 09/484,402, filed on Jan. 14, 2000, now Pat. No. 6,221,892, which is a division of application No. 09/023,147, filed on Feb. 12, 1998, now Pat. No. 6,063,801.

(51) Int. Cl.$^7$ .................. A61K 31/4184; C07D 403/04

(52) U.S. Cl. ..................... 514/394; 548/305.4

(58) Field of Search ............... 548/305.4; 514/394

(56) References Cited

U.S. PATENT DOCUMENTS

| 2,985,661 A | 5/1961 | Hien et al. ............ 260/309 |
| RE26,065 E | 7/1966 | Marvel et al. ........... 260/47 |
| 3,449,330 A | 6/1969 | Guglielmetti et al. ..... 260/240 |
| 3,538,097 A | 11/1970 | Lowe et al. ............ 260/268 |
| 4,938,949 A | 7/1990 | Borch et al. ............ 424/10 |
| 5,106,863 A | 4/1992 | Hajos et al. ............ 514/395 |
| 5,112,532 A | 5/1992 | Ninomiya et al. ........ 252/587 |
| 5,126,351 A | 6/1992 | Luzzio et al. .......... 514/291 |
| 5,244,903 A | 9/1993 | Wall et al. ............ 514/279 |
| 5,318,976 A | 6/1994 | Luzzi et al. ........... 514/279 |
| 5,767,142 A | 6/1998 | La Voie et al. ......... 514/394 |
| 5,770,617 A | 6/1998 | LaVoie et al. .......... 514/394 |
| 5,807,874 A | 9/1998 | LaVoie et al. .......... 514/338 |
| 5,948,797 A | 9/1999 | La Voie et al. ......... 514/338 |
| 6,063,801 A * | 5/2000 | LaVoie et al. .......... 514/394 |

FOREIGN PATENT DOCUMENTS

| EP | 0496634 | 7/1992 | ...... C07D/491/056 |
| SU | 1530628 | 12/1989 | ...... C07D/235/20 |
| WO | 92/21661 | 12/1992 | ...... C07D/221/18 |
| WO | 96/36612 | 11/1996 | ...... C07D/235/18 |
| WO | 97/29106 | 8/1997 | ...... C07D/455/02 |
| WO | 98/12181 | 3/1998 | ...... C07D/221/18 |
| WO | 98/31673 | 7/1998 | ...... C07D/235/18 |

OTHER PUBLICATIONS

International PCT Search Report for PCT/US 98/01005, 5 pgs, (Jun. 22, 1998).

Aquirre, J.M., et al., "Reaction of 1,2–diarylethylamides with ethyl polyphosphate(EPP): correlation of the von Braun, Ritter and Bischler–Napieralski reactions", *Chemical Abstracts*, 111 (13), Abstract No. 115004, pp. 25–27, (Sep. 25, 1989).

Badia, D., et al., "Silicon–mediated isoquinoline synthesis: preparation and stereochemical characterization of 4–hydroxy–3–phenylisoquinolines", *Chemical Abstracts*, 117 (13), Abstract No. 131034, p. 730, (Sep. 28, 1992).

Bradsher, C.K., et al., ".alpha–Acyl–o–tolunitriles as imtermediates in the preparation of 3–substituted isoquinolines and 1–amino–2–benzopyrylium derivatives", *Chemical Abstracts*, 089 (21), Abstract No. 179810, pp. 3817–3820, (1978).

Chen, A.Y., et al., "A New Mammalian DNA Topoisomerase I Poison Hoechst 33342: Cytoxicity and Drug Resistance in Human Cell Cultures", *Cancer Research*, 53 (6), pp. 1332–1337, (Mar. 15, 1993).

Chen, A.Y., et al., "DNA Minor Groove–Binding Ligands: A Different Class of Mammalian DNA Topoisomerase I Inhibitors", *Proc. Natl. Acad. Sci.*, USA, 90, pp. 8131–8135, (Sep. 1993).

Chen, A.Y., et al., "DNA Topoisomerases: Essential Enzymes and Lethal Targets", *Annu. Rev. Pharmacol. Toxicol.*, 34, pp. 191–218, (1994).

Cherif, A., et al., "N–(5, 5–Diacetoxypent–1–yl)doxorubicin: A New Intensely Potent Doxorubicin Analogue", *J. Med. Chem.*, 35, pp. 3208–3214, (1992).

(List continued on next page.)

Primary Examiner—Laura L. Stockton
(74) Attorney, Agent, or Firm—Schwegman, Lundberg, Woessner & Kluth, P.A.

(57) ABSTRACT

The invention provides a topoisomerase poison of formula I:

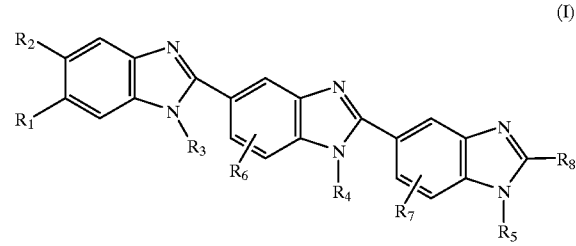

(I)

wherein $R_1$-$R_8$ have any of the meanings defined in the specification, or a pharmaceutically acceptable salt thereof, as well as pharmaceutical compositions comprising a compound of formula I or a salt thereof, intermediates useful for preparing a compound of formula I, and therapeutic methods comprising administering a compound of formula I or a salt thereof.

31 Claims, 2 Drawing Sheets

OTHER PUBLICATIONS

Croisy–Delcey, M., et al., "Synthesis and Carcinogenic Activity of Oxidized Benzacridines: Potential Metabolites of the Strong Carcinogen 7–MEthylbenz(c)acridine and of the Inactive Isomer 12–Methylbenz(a)acridine", *American Chemical Society,* 26 (2), pp. 303–306, (1983).

D'arpa, P., et al., "Topoisomerase–Targeting Antitumor Drugs", *Biochimica et Biophysica Acta,* 989, pp. 163–177, (1989).

Dominguez, E., et al., "Dehydrogenation reactions of 1–substituted–3–aryltetrahydroisoquin oline derivatives", *Chemical Abstracts,* 101 (11), Abstract No. 090742, pp. 525–528, (1984).

Dorofeenko, G.N., et al., "Synthesis of 3–aryl derivatives of 2–benzopyrylium salts with free.alpha–positions", *Chemical Abstracts,* 074 (15), Abstract No. 076295, pp. 1013–1014, (1971).

Fitzgerald, J.J., et al., "Reaction of benzocyclobutene oxides with nitriles: synthesis of hypercumine and other 3–substituted isoquinolines", *Chemical Abstracts,* 122 (7), Abstract No. 081704, p. 1128, (Feb. 13, 1995).

Fox, G.J., et al., "para–Bromination of Aromatic Amines: 4–Bromo–N,N–Dimethyl–3–(Trifluoromethyl)Aniline", *Organic Synthesis,* 55, pp. 20–23, (1973).

Fujii, N., et al., "Induction of Mammalian DNA Topoisomerase I–mediated DNA Cleavage and DNA Winding by Bulgarein", *Journal of Biological Chemistry,* 268, pp. 13160–13165, (1993).

Gallo, R.C., et al., "Studies on the Antitumor Activity, Mechanism of Action, and Cell Cycle Effects of Camptothecin", *Journal of the National Cancer Institute,* 46, pp. 789–795, (Apr. 1971).

Gandhi, K.K., et al., "Regioselective thermal cyclization of 3–substituted arylenaminoimine hydrochlorides, a convenient method for the synthesis of functionalized polycyclic quinoline derivatives", *Heterocycles,* 41 (5), pp. 911–920, (1995).

Garcia, A., et al., "A simple direct approach to 1–substituted 3–arylisoquinolines from deoxybenzoins and nitriles", *Chemical Abstracts,* 110 (25), Abstract No. 231407, pp. 6681–6686, (Jun. 19, 1989).

Gatto, B., et al., "Identification of Topoisomerase I as the Cyctotoxic Target of the Protoberberine Alkaloid Coralyne", *Cancer Research,* 56, pp. 2795–2800, (1996).

Giovanella, B.C., et al., "Complete Growth Inhibition of Human Cancer Xenografts in Nude Mice by Treatment with 20–(S)—Camptothecin", *Cancer Research,* 51, pp. 3052–3055, (Jun. 1, 1991).

Goldman, G.H., et al., "Differential poisoning of humand and *aspergilus nidulans* DNA topoisomerase I by Bi– and Terbenzimidazoles", *Biochemistry,* 36 (21), pp. 6488–6494, (1997).

Hoan, N., et al., "Syntheses from o–halogenated anisoles and phenetoles", *Chemical Abstracts,* 41 (20), Abstract No. 6571bg, 1 p., (1947).

Iwao, M., et al., "A Regiospecific Synthesis of Carbazones via Consecutive Palladium–Catalyzed Cross–coupling and Aryne–Mediated Cyclization", *Heterocycles,* 36, pp. 1483–1488, (1993).

Janin, Y.L., et al., "Synthesis and Evaluation of New 6–Amino–Substituted Benzo[c]phenanthridine Derivatives", *J. Med. Chem,* 36 (23), pp. 3686–3692, (1993).

Kametani, T., et al., "Studies on the synthesis of heterocyclic compounds. DCXXVII. The formation of 2,3,9,10–tetramethoxybenz[c]acridine by treatment of 6,7–dimethoxy–1–(4,5–dimethoxy–2–nitrophen ethyl)–2methylisoquinoline with triethyl phosphite", *Chemical and Pharmaceutical Bulletin,* 23 (9), pp. 2025–2028, (1975).

Kim, J.S., et al., "Influence of steric factors on topoisomerase I inhibition and cytotoxicity of bisbenzimidazoles related to Hoechst 33342", *Abstract 7—Proceedings of the 3rd Annual Scientific Retreat of the Cancer Institute of New Jersey,* Princeton Marrtott Forrestal Village, p. 28, (1995).

Kim, J.S., et al., "Influence of steric factors on topoisomerase I inhibition and cytotoxicity of bisbenzimidazoles related to Hoechst 33342", *Proceedings of the 86th Annual Meeting of the American Association for Cancer Research,* 36, Abstract No. 2689, Toronto, Ontario, Canada, p. 451, (Mar. 1995).

Kim, J.S., et al., "Quantitative structure–activity relationships on 5–substituted terbenzimidazoles as topoisomerase I poisons and antitumor agents", *Bioorg. Med. Chem.,* 6 (2), pp. 163–172, (1998), CA 128:278724.

Kim, J.S., et al., "Steric factors associated with the topoisomerase I inhibition and cytotoxicity of substituted bisbenzimidazoles", *Abstract 10– Proceedings of the American Association of Pharmaceutical Scientists Eastern Regional Meeting,* p. 27, (1995).

Kim, J.S., et al., "Structure–activity Relationships of Benzimidazoles and Related Heterocycles as Topoisomerase I Poisons", *BIoorganic & Med. Chem.,* 4, pp. 621–630, (1996).

Kim, J.S., et al., "Substituted 2,5'–Bi–1H–benzimidazoles: Topoisomerase I Inhibition and Cytotoxicity", *J. Med. Chem.,* 39, pp. 992–998, (1996).

Kim, J.S., et al., "Terbenzimidazoles: influence of 2"–, 4–, and 5–substituents on cytotoxicity and relative potency as topoisomerase I poisons", *J. Med. Chem.,* 40, pp. 2818–2821, (1997).

Kitamura, T., et al., "Isoquinoline derivatives from the Ritter–type reaction of vinyl cations", *Chemical Abstracts,* 102 (1), Abstract No. 006157, pp. 1351–1354, (Jan. 7, 1985).

LaVoie, E.J., et al., "Structure–activity studies related to minor groove–binding ligands which inhibit mammalian DNA topoisomerase I", *Abstract 1—Proceedings of the 85th Annual Meeting of American Association for Cancer Research,* San Francisco, CA, p. 2699, (Apr. 1994).

Makhey, D., et al., "Coralyne and Related Compounds as Mammalian Topoisomerase I and Topoisomerase II Poisons", *Bioorg. & Med. Chem. Lett.,* 4, pp. 781–791, (1996).

Makhey, D., et al., "Protoberberine Alkaloids and Related Compounds as Dual Inhibitors of Mammalian Topoisomerase I and II", *Med Chem. Res.,* 5, pp. 1–12, (1994).

Meegalla, S.K., et al., "Synthesis and Pharmacological Evaluation of Isoindolo[1,2–b]quinazolinone and Isoindolo [2,1–a]benzimidazole Derivatives Related to the Antitumor Agent Batracylin", *J. Med. Chem.,* 37, pp. 3434–3439, (1994).

Memetzidis, G., et al., "Structure–affinity relationships of berbines or 5,6,13,13a–tetrahydro–8H–dibenzo[a,g]quino lizines at.alpha.–adrenoceptors", *Eur. J. Med. Chem.,* 26, pp. 605–611, (1991).

Nelson, J.T., et al., "Proton and carbon–13 NMR spectra of fifteen substituted isoquinolines", *Chemical Abstracts,* 115 (5), Abstract No. 048721, 1 p., (Aug. 5, 1991).

Peters, D., et al., "Synthesis of Various 5–Substituted Uracils", *J. Heterocyclic Chem.*, 27, pp. 2165–2173, (Nov./Dec. 1990).

Pilch, D.S., et al., "A terbenzimidazole that preferentially binds and conformationally alters structurally distinct DNA duplex domains: a potential mechanism for topoisomerase I poisoning", *Proc. Nat'l. Acad. Sci.*, USA, 94, pp. 13565–13570, (Dec. 1997).

Pilch, D.S., et al., "Biophysical Characterization of a Cytotoxic, Topoisomerase I Poison", *Abstract 8—Proceedings of the 3rd Annual Scientific Retreat of the Cancer Institute of New Jersey*, Princeton Marriott Forrestal Village, Princeton, NJ, p. 3, (Jun. 1, 1995).

Pilch, D.S., et al., "Characterizing the DNA binding modes of a topoisomerase I–poisoning terbenzimidazole: evidence for both intercalative and minor groove binding properties", *Drug Design and Discovery*, 13, pp. 115–133, (1996).

Piper, J.R., et al., "Synthesis and Antifolate Activity of 5–Methyl–5,10–dideaza Analogues of Aminopterin and Folic Acid and an Alternative Synthesis of 5,10–Dideaza-tetrahydrofolic Acid, a Potent Inhibitor of Glycinamide Ribonucleotide Formyltransferase", *J. Med. Chem.*, 31, pp. 2164–2169, (1988).

Porai–Koshits, B.A., et al., "Imidazole derivatives Synthesis of some polybenzimidazoles", *J. Gen. Chem. USSR*, 23, As related in Chemical Abstracts, 48 (10) (1954), col. 12740, pp. 873–879, (1953).

Porai–Koshits, B.A., et al., "Imidazole derivatives. Synthesis of some polybenzimidazoles", *Zhur. Obshchei Khim*, 23, As related in Chemical Abstracts, 48 (1954) col. 4523, pp. 835–841, (1953).

Quast, U., et al., "Heterocyclic.alpha.–carbinolamines with theisoquinuclidine skeleton. 3. Benzoisoquinuclidines", *Chemical Abstracts*, 097 (21), Abstract No. 182180, pp. 1501–1508, (1982).

Safaryan, G.P., et al., "2–Benzopyrylium salts. 25, Reaction of 2–benzopyrylium salts with some nucleophiles", *Chemical Abstracts*, 096 (17), Abstract No. 142656, pp. 1608–1611, (1982).

Schiess, P., et al., "Thermolytic ring opening of acyloxy-benzocyclobutenes: an efficient route to 3–substituted iso-quinolines", *Chemical Abstracts*, 104 (19), Abstract No. 168332, pp. 3959–3962, (May 12, 1986).

Shcherbakova, I.V., et al., "2–Benzopyrilium salts.35.Synthesis of the natural alkaloid dehydronorcoraly-dine and other substituted salts of dibenzo {a,g}quinolizine", *Chemical Abstracts*, 112 (19), Abstract No. 179554, pp. 75–80, (May 7, 1990).

Singh, M.P., et al., "Synthesis and Sequence–Specific DNA Binding of a Topoisomerase Inhibitory Analog of Hoechst 33258 Designed for Altered Base and Sequence Recognition", *Chem. Res. Toxicol.*, 5, pp. 597–607, (1992).

Sotomayor, N., et al., "Oxidation reactions of 2'–functionalized 3–aryltetrahydro–and 3,4–dihydroisoquinolines", *Chemical Abstracts*, 124 (11), Abstract No. 145854, p. 1227, (Mar. 11, 1996).

Stermitz, F.R., et al., "Synthesis and Biological Activity of Some Antitumor Benzophenanthridinum Salts", *Journal of Medicinal Chemistry*, 18, pp. 708–713, (1975).

Sun, et al., *Chemical Abstracts*, 123 (15), Abstract No. 198740r, 1 p., (1995).

Sun, Q., et al., "Structure activity of novel topoisomerase I inhibitors related to Hoechst 33342", *Abstract 6—Proceedings of the American Association of Pharmaceutical Scientists Eastern Regional Meeting*, Hyatt Regency Hotel, New Brunswick, NJ, p. 25, (Jun. 5–6, 1995).

Sun, Q., et al., "Structure Activity of Topoisomerase I Poisons related to Hoechst 33342", *Bioorganic & Medicinal Chemistry Letters*, vol. 4, No. 24, pp. 2871–2876, (1994).

Sun, Q., et al., "Structure–activity studies related to minor groove–binding ligands which inhibit mammalian DNA topoisomerase I", *Cancer Institute of New Jersey's First Annual Scientific Retreat*, Abstract 2, Princeton Marriott Forrestal Village, Princeton, NJ, p. 66, (Jun. 7, 1994).

Sun, Q., et al., "Synthesis and Evaluation of Terbenzimidazoles as Topoisomerase I Inhibitors", *Chemical Abstracts*, 123 (15), Abstract No.198740r, p. 1241, (1995).

Sun, Q., et al., "Synthesis and Evaluation of Terbenzimidazoles as Topoisomerase I Inhibitors", *J. Med. Chem*, vol. 38, pp. 3638–3644, (1995).

Sun, Q., et al., "Synthesis and pharmacological evaluation of a series of novel DNA topoisomerase I inhibitors as antitumor agents", *Abstract 5—Proceedings of the 3rd Annual Scientific Retreat of the Cancer Institute of New Jersey*, Princeton Marriott Forrestal Village, Princeton, NJ, p. 27, (1995).

Sun, Q., et al., "Synthesis and pharmacological evaluation of a series of novel DNA topoisomerase I inhibitors as antitumor agents", *Proceedings of the 86th Annual Meeting of the American Association for Cancer Research*, Toronto, Ontario, Canada, p. 2688, (1995).

Sun, Q., et al., "Synthesis and Pharmacological Evaluation of a Series of Novel DNA Topoisomerase I Inhibitors as Antitumor Agents", *Scientific Proceedings of 86th Annual Meeting of the American Association for Cancer Research*, Abstract 3, Toronto, Canada, 1 p., (Mar. 18–22, 1995).

Sun, Q., et al., "Synthesis of Benzimidazo[2,1–a]isoquinolines and 5,6–Dihydrobenzimidazo[2,1–a]isoquinolines", *Syn. Lett.*, submitted, Paper No. 7, 6 p., (1995).

Vinogradov, A.E., et al., "Some properties of new DNA specific bisbenzimidazole fluorochromes without a piperzine ring", *Biotechnic & Histochemistry*, 38 (5), pp. 265–269, (1993).

Walterova, D., et al., "Isolation, Chemistry and Biology of Alkaloids from plants of Papaveraceae. Part XCV. Practical application of isotachophoresis in analysis of isoquinoline alkaloids", *Chemical Abstract*, 104 (12), pp. 23–36, (1986), CA 104:95573s.

Wang, L., et al., "Inhibition of Topoisomerase I Function by Coralyne and 5,6 –Dihydrocoralyne", *Chem. Res. Toxicol.*, 9, pp. 75–83, (1996).

Wang, L., et al., "Inhibition of Topoisomerase I Function by Nitidine and Fagaronine", *Chem. Res. Toxicol.*, 6, pp. 813–818, (1993).

Yadagiri, B., et al., "Convenient Routes to Substituted Benzimidazoles and Imidazolo[4,5–b]Pyridines Using Nitrobenzene as Oxidant", *Synthetic Communications*, 20 (7), pp. 955–963, (1990).

Yamamoto, Y., et al., "Reaction of 6H–1, 3–oxazin–6–one with benzyne giving isoquinoline derivatives", *Chemical Abstracts*, 118 (7), Abstract No. 059563, 2 p., (Feb. 15, 1993).

Yamashita, Y., et al., "Induction of Mammalian DNA Topoisomerase I and II Mediated DNA Cleavage by Saintopin, a New Antitumor Agent from Fungus", *Biochemistry*, 30, pp. 5838–5845, (1991).

Yamashita, Y., et al., "Induction of Mammalian DNA Topoisomerase I Mediated DNA Cleavage by Antitumor Indolo-carbazole Derivatives", *Biochemistry*, 31, pp. 12069–12075, (1992).

\* cited by examiner

FIGURE 1

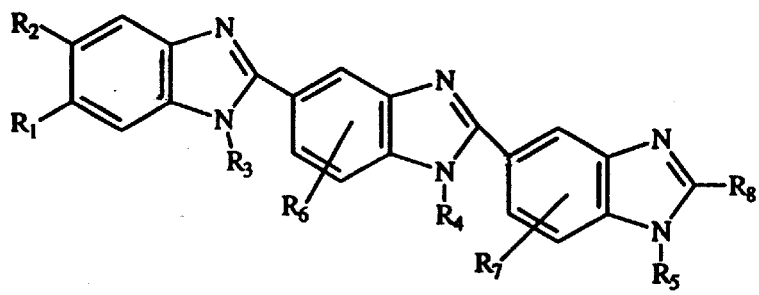

(I)

| Compound | $R_1$ | $R_2$ | $R_3$ | $R_4$ | $R_5$ | $R_6$ | $R_7$ | $R_8$ |
|---|---|---|---|---|---|---|---|---|
| 1 | H | Phenyl | H | H | H | H | H | H |
| 2 | H | Phenyl | H | H | H | H | H | OH |
| 3 | H | Phenyl | H | H | H | H | H | SH |
| 4 | H | Phenyl | H | H | H | H | H | $NH_2$ |
| 5 | H | Phenyl | H | H | H | H | H | $CF_3$ |
| 6 | H | Phenyl | H | H | H | H | H | $CH_3$ |
| 7 | H | Phenyl | H | H | H | H | H | $CH_2OH$ |
| 8 | H | Phenyl | H | H | H | H | H | $CH_2NHCOC_6H_5$ |
| 9 | H | Phenyl | H | H | H | H | H | $CH_2CH_3$ |
| 10 | H | Phenyl | H | H | H | H | H | $(CH_2)_2OH$ |
| 11 | H | Phenyl | H | H | H | H | H | $(CH_2)_2NH_2$ |
| 12 | H | Phenyl | H | H | H | H | H | $(CH_2)_2NHCOCH_3$ |
| 13 | H | Phenyl | H | H | H | H | H | $(CH_2)_2OCH_3$ |
| 14 | H | Phenyl | H | H | H | H | H | $(CH_2)_2CH_3$ |
| 15 | Phenyl | $OCH_3$ | H | H | H | H | H | H |
| 16 | Phenyl | Phenyl | H | H | H | H | H | H |
| 17 | H | Br | H | H | H | H | H | H |
| 18 | H | Br | H | H | H | H | H | OH |
| 19 | H | Br | H | H | H | H | H | $(CH_2)_2CH_3$ |
| 20 | Br | Br | H | H | H | H | H | H |
| 21 | $OCH_3$ | Br | H | H | H | H | H | H |
| 22 | Br | Br | H | H | H | H | H | $CF_3$ |

| Compounds | Topo-I mediated DNA cleavage | Cytotoxicity (μg/ml) RPMI 8402 | Cytotoxicity (μg/ml) CPT-K5 | Cytotoxicity (μg/ml) U937 | Cytotoxicity (μg/ml) U/CR |
|---|---|---|---|---|---|
| 1 | 0.01 | 0.07 | 0.33 | 0.025 | 0.023 |
| 2 | 0.1 | 0.09 | 0.28 | 0.02 | 0.03 |
| 3 | 0.01 | 0.06 | 0.33 | 0.025 | 0.02 |
| 4 | 1.0 | >10 | >10 | | |
| 5 | <0.01 | 0.02 | >10 | 0.006 | 0.01 |
| 6 | 0.02 | 0.11 | N.D. | N.D. | N.D. |
| 7 | 0.1 | 0.09 | >10 | 0.025 | 0.035 |
| 8 | 0.1 | 5 | >10 | 5.5 | 5.5 |
| 9 | 0.01 | 0.11 | N.D. | N.D. | N.D. |
| 10 | 0.005 | 1.2 | >10 | 0.45 | 0.5 |
| 11 | 0.1 | 4 | >10 | 3 | 3.5 |
| 12 | 0.01 | 0.05 | >50 | 0.3 | 0.035 |
| 13 | 0.1 | 0.18 | >10 | 0.055 | 0.06 |
| 14 | 0.005 | 0.06 | N.D. | N.D. | N.D. |
| 15 | N.D. | N.D. | | | |
| 16 | 0.01 | N.D. | | | |
| 17 | 0.01 | 1.4 | N.D. | N.D. | N.D. |
| 18 | <0.01 | 1.5 | 0.09 | 0.7 | 0.75 |
| 19 | 0.01 | 0.3 | 2.0 | 0.3 | 0.25 |
| 20 | 0.005 | 0.2 | 0.25 | 0.06 | 0.15 |
| 21 | N.D. | N.D. | | | |
| 22 | N.D. | N.D. | | | |

Figure 2

BENZIMIDAZOLE TOPOISOMERASE POISONS

This application is a Continuation of U.S. patent application Ser. No. 09/484,402, filed on Jan. 14, 2000 now U.S. Pat. No. 6,221,892, which is a Division of U.S. patent application Ser. No. 09/023,147, filed on Feb. 12, 1998, now issued U.S. Pat. No. 6,063,801, issued on May 16, 2000.

GOVERNMENT FUNDING

The invention described herein was made with government support under grant CA-39662 awarded by the National Cancer Institute. The United States Government has certain rights in the invention.

BACKGROUND OF THE INVENTION

DNA-topoisomerases are enzymes present in the nuclei of cells where they catalyze the breaking and rejoining of DNA strands, controlling the topological state of DNA. Recent studies also suggest that topoisomerases are involved in regulating template supercoiling during RNA transcription. There are two major classes of mammalian topoisomerases. DNA-topoisomerase-I catalyzes changes in the topological state of duplex DNA by performing transient single-strand breakage-union cycles. In contrast, mammalian topoisomerase II alters the topology of DNA by causing a transient enzyme bridged double-strand break, followed by strand passing and resealing. Mammalian topoisomerase II has been further classified as Type II α and Type II β. The antitumor activity associated with agents which are topoisomerase poisons is associated with their ability to stabilize the enzyme-DNA cleavable complex. This drug-induced stabilization of the enzyme-DNA cleavable complex effectively converts the enzyme into a cellular poison.

Several antitumor agents in clinical use have potent activity as mammalian topoisomerase II poisons. These include adriamycin, actinomycin D, daunomycin, VP-16, and VM-26 (teniposide or epipodophyllotoxin).

In contrast to the number of clinical and experimental drugs which act as topoisomerase II poisons, there are currently only a limited number of agents which have been identified as topoisomerase I poisons. Camptothecin and its structurally-related analogs are among the most extensively studied topoisomerase I poisons. Recently, bi- and terbenzimidazoles (Chen et al., *Cancer Res.* 1993, 53, 1332–1335; Sun et al., *J. Med. Chem.* 1995, 38, 3638–3644; Kim et al., *J Med. Chem.* 1996, 39, 992–998), certain benzo[c] phenanthridine and protoberberine alkaloids and their synthetic analogs (Makhey et al., *Med. Chem. Res.* 1995, 5, 1–12; Janin et al., *J. Med. Chem* 1975, 18, 708–713; Makhey et al., *Bioorg. & Med. Chem.* 1996, 4, 781–791), as well as the fungal metabolites, bulgarein (Fujii et al., *J. Biol. Chem.* 1993, 268, 13160–13165) and saintopin (Yamashita et al., *Biochemistry* 1991, 30, 5838–5845) and indolocarbazoles (Yamashita et al., *Biochemistry* 1992, 31, 12069–12075) have been identified as topoisomerase I poisons.

Presently, a need exists for novel anti-cancer agents, for anti-cancer agents that exhibit improved activity, and for anti-cancer agents that exhibit fewer side-effects or improved selectivity compared to existing agents.

SUMMARY OF THE INVENTION

The present invention provides compounds that exhibit inhibitory activity against topoisomerase I, and compounds that are effective cytotoxic agents against cancer cells, including drug-resistant cancer cells. Accordingly there is provided a compound of the invention which is a compound of formula I:

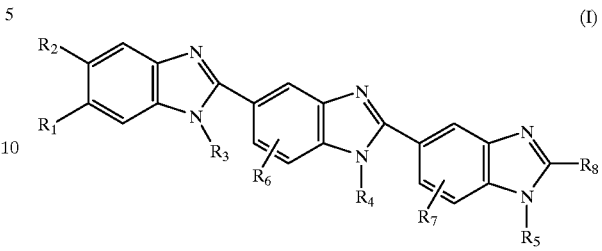

wherein $R_1$ and $R_2$ are each independently hydrogen, $(C_1-C_6)$ alkyl, $(C_3-C_6)$cycloalkyl, $(C_3-C_6)$cycloalkyl$(C_1-C_6)$alkyl, $(C_1-C_6)$ alkoxy, $(C_3-C_6)$cycloalkyl$(C_1-C_6)$alkoxy, hydroxy, halo, nitro, cyano, mercapto, carboxy, hydroxy$(C_1-C_6)$alkyl, halo$(C_1-C_6)$alkyl, trifluoromethoxy, $(C_1-C_6)$alkanoyl, $(C_1-C_6)$alkoxycarbonyl, $(C_1-C_6)$alkylthio, $(C_1-C_6)$alkanoyloxy, aryl, heteroaryl, aryl$(C_1-C_6)$alkyl, or heteroaryl$(C_1-C_6)$alkyl; or $R_1$ and $R_2$ taken together are methylenedioxy; or $R_1$ and $R_2$ taken together are benzo;

$R_3$, $R_4$, and $R_5$ are each independently selected from the group consisting of hydrogen, $(C_1-C_6)$alkyl, $(C_3-C_6)$cycloalkyl, $(C_1-C_6)$alkanoyl, $(C_1-C_6)$alkoxycarbonyl, $(C_2-C_6)$alkanoyloxy, aryl, heteroaryl, aryl$(C_1-C_6)$alkyl, and heteroaryl$(C_1-C_6)$alkyl;

$R_6$ and $R_7$ are each independently hydrogen, $(C_1-C_6)$ alkyl, $(C_3-C_6)$cycloalkyl, $(C_3-C_6)$cycloalkyl$(C_1-C_6)$alkyl, $(C_1-C_6)$alkoxy, $(C_3-C_6)$cycloalkyl$(C_1-C_6)$alkoxy, hydroxy, halo, nitro, cyano, mercapto, carboxy, hydroxy$(C_1-C_6)$alkyl, halo$(C_1-C_6)$akyl, trifluoromethoxy, $(C_1-C_6)$alkanoyl, $(C_1-C_6)$alkoxycarbonyl, $(C_1-C_6)$alkylthio, or $(C_1-C_6)$alkanoyloxy;

$R_8$ is hydroxy, halo, nitro, cyano, mercapto, carboxy, $(C_1-C_6)$alkoxy, $(C_3-C_6)$cycloalkyl$(C_1-C_6)$alkoxy, —$NR_aR_b$, halo$(C_1-C_6)$alkyl, trifluoromethoxy, $(C_1-C_6)$alkanoyl, $(C_1-C_6)$alkoxycarbonyl, $(C_1-C_6)$alkylthio, $(C_1-C_6)$alkanoyloxy, aryloxy, or heteroaryloxy; or $R_8$ is $(C_1-C_6)$alkyl substituted by 1, 2, or 3 substituents independently selected from the group consisting of hydroxy, nitro, cyano, mercapto, carboxy, $(C_1-C_6)$alkoxy, $(C_3-C_6)$cycloalkyl$(C_1-C_6)$alkoxy, —$NR_aR_b$, trifluoromethoxy, $(C_1-C_6)$alkanoyl, $(C_1-C_6)$ alkoxycarbonyl, $(C_1-C_6)$alkylthio, $(C_1-C_6)$alkanoyloxy, aryloxy, and heteroaryloxy; and each of $R_a$ and $R_b$ is independently hydrogen, $(C_1-C_6)$ alkyl, $(C_1-C_6)$alkanoyl, $(C_1-C_6)$alkoxycarbonyi, aryl, heteroaryl, aryl$(C_1-C_6)$alkyl, heteroaryl$(C_1-C_6)$alkyl, arylcarbonyl, or heteroarylcarbonyl; or $R_a$ and $R_b$ together with the nitrogen to which they are attached are pyrrolidino, piperidino, or morpholino.

wherein any aryl, heteroaryl, or benzo of $R_1$-$R_5$, $R_8$, $R_a$, and $R_b$ may optionally be substituted by 1, 2, or 3 substituents independently selected from the group consisting of $(C_1-C_6)$alkyl, $(C_3-C_6)$cycloalkyl, $(C_3-C_6)$cycloalkyl$(C_1-C_6)$ alkyl, $(C_1-C_6)$alkoxy, $(C_3-C_6)$cycloalkyl$(C_1-C_6)$alkoxy, hydroxy, halo, nitro, cyano, mercapto, carboxy, hydroxy$(C_1-C_6)$alkyl, halo$(C_1-C_6)$alkyl, trifluoromethoxy, $(C_1-C_6)$alkanoyl, $(C_1-C_6)$alkoxycarbonyl, $(C_1-C_6)$alkylthio, and $(C_1-C_6)$alkanoyloxy;

or a pharmaceutically acceptable salt thereof.

The invention also provides a compound of the invention which is a compound of formula I:

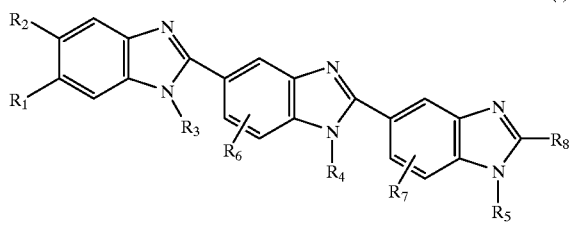

wherein $R_1$ and $R_2$ are each independently $(C_1-C_6)$alkyl, $(C_3-C_6)$cycloalkyl, $(C_3-C_6)$cycloalkyl$(C_1-C_6)$alkyl, $(C_1-C_6)$alkoxy, $(C_3-C_6)$cycloalkyl$(C_1-C_6)$alkoxy, hydroxy, halo, nitro, cyano, mercapto, carboxy, hydroxy$(C_1-C_6)$alkyl, halo$(C_1-C_6)$alkyl, trifluoromethoxy, $(C_1-C_6)$alkanoyl, $(C_1-C_6)$alkoxycarbonyl, $(C_1-C_6)$alkylthio, $(C_1-C_6)$alkanoyloxy, aryl, heteroaryl, aryl$(C_1-C_6)$alkyl, or heteroaryl$(C_1-C_6)$alkyl; or $R_1$ and $R_2$ taken together are methylenedioxy;

$R_3$, $R_4$, and $R_5$ are each independently selected from the group consisting of hydrogen, $(C_1-C_6)$alkyl, $(C_3-C_6)$cycloalkyl, $(C_1-C_6)$alkanoyl, $(C_1-C_6)$alkoxycarbonyl, $(C_2-C_6)$alkanoyloxy, aryl, heteroaryl, aryl$(C_1-C_6)$alkyl, and heteroaryl$(C_1-C_6)$alkyl;

$R_6$ and $R_7$ are each independently hydrogen, $(C_1-C_6)$alkyl, $(C_3-C_6)$cycloalkyl, $(C_3-C_6)$cycloalkyl$(C_1-C_6)$alkyl, $(C_1-C_6)$alkoxy, $(C_3-C_6)$cycloalkyl$(C_1-C_6)$alkoxy, hydroxy, halo, nitro, cyano, mercapto, carboxy, hydroxy$(C_1-C_6)$alkyl, halo$(C_1-C_6)$alkyl, trifluoromethoxy, $(C_1-C_6)$alkanoyl, $(C_1-C_6)$alkoxycarbonyl, $(C_1-C_6)$alkylthio, or $(C_1-C_6)$alkanoyloxy; and $R_8$ is hydrogen, $(C_1-C_6)$alkyl, aryl, or heteroaryl;

wherein any aryl or heteroaryl of $R_1$-$R_5$ and $R_8$ may optionally be substituted by 1, 2, or 3 substituents independently selected from the group consisting of $(C_1-C_6)$alkyl, $(C_3-C_6)$cycloalkyl, $(C_3-C_6)$cycloalkyl$(C_1-C_6)$alkyl, $(C_1-C_6)$alkoxy, $(C_3-C_6)$cycloalkyl$(C_1-C_6)$alkoxy, hydroxy, halo, nitro, cyano, mercapto, carboxy, hydroxy$(C_1-C_6)$alkyl, halo$(C_1-C_6)$alkyl, trifluoromethoxy, $(C_1-C_6)$alkanoyl, $(C_1-C_6)$alkoxycarbonyl, $(C_1-C_6)$alkylthio, and $(C_1-C_6)$alkanoyloxy;

or a pharmaceutically acceptable salt thereof.

The invention also provides a pharmaceutical composition comprising a compound of formula I, or a pharmaceutically acceptable salt thereof, in combination with a pharmaceutically acceptable carrier.

The invention also provides a therapeutic method comprising inhibiting cancer cells by administering to a mammal (e.g. a human) in need of such therapy, an amount of a compound of formula I, or a pharmaceutically acceptable salt thereof, effective to inhibit said cancer cells.

The invention also provides a method comprising inhibiting cancer cells by contacting said cancer cells in vitro or in vivo with an amount of a compound of formula I, or a pharmaceutically acceptable salt thereof, effective to inhibit said cancer cells, i.e. to inhibit their activity, such as their ability to divide, migrate, or proliferate.

The invention also provides a compound of formula I for use in medical therapy (preferably for use in treating cancer, e.g. solid tumors; or for use as an antifungal agent), as well as the use of a compound of formula I for the manufacture of a medicament useful for the treatment of cancer, e.g. solid tumors, and the use of a compound of formula I for the manufacture of a medicament useful for the treatment of fungal infeaction.

The invention also provides processes and novel intermediates disclosed herein which are useful for preparing compounds of the invention. Some of the compounds of formula I are useful to prepare other compounds of formula I.

BRIEF DESCRIPTION OF THE FIGURES

FIG. 1 shows the structure of representative compounds of the invention and other compounds (1, 6, 9, 14, 17, and 19).

FIG. 2 shows biological data for representative compounds of formula I.

DETAILED DESCRIPTION

The following definitions are used, unless otherwise described: halo is fluoro, chloro, bromo, or iodo. Alkyl, alkoxy, etc. denote both straight and branched groups; but reference to an individual radical such as "propyl" embraces only the straight chain radical, a branched chain isomer such as "isopropyl" being specifically referred to. Aryl denotes a phenyl radical or an ortho-fused bicyclic carbocyclic radical having about nine to ten ring atoms in which at least one ring is aromatic. Heteroaryl encompasses a radical attached via a ring carbon of a monocyclic aromatic ring containing five or six ring atoms consisting of carbon and one to four heteroatoms each selected from the group consisting of non-peroxide oxygen, sulfur, and N(Y) wherein Y is absent or is H, O, $(C_1-C_4)$alkyl, phenyl or benzyl, as well as a radical of an ortho-fused bicyclic heterocycle of about eight to ten ring atoms derived therefrom, particularly a benzo-derivative or one derived by fusing a propylene, trimethylene, or tetramethylene diradical thereto.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine topoisomerase poisoning activity or cytotoxic activity using the standard tests described herein, or using other similar tests which are well known in the art.

Specific and preferred values listed below for radicals, substituents, and ranges, are for illustration only; they do not exclude other defined values or other values within defined ranges for the radicals and substituents Specifically, $(C_1-C_6)$alkyl can be methyl, ethyl, propyl, isopropyl, butyl, isobutyl, sec-butyl, pentyl, 3-pentyl, or hexyl; $(C_3-C_6)$cycloalkyl can be cyclopropyl, cyclobutyl, cyclopentyl, or cyclohexyl; $(C_3-C_6)$cycloalkyl$(C_1-C_6)$alkyl can be cyclopropylmethyl, cyclobutylmethyl, cyclopentylmethyl, cyclohexylmethyl, 2-cyclopropylethyl, 2-cyclobutylethyl, 2-cyclopentylethyl, or 2-cyclohexylethyl; $(C_1-C_6)$alkoxy can be methoxy, ethoxy, propoxy, isopropoxy, butoxy, isobutoxy, sec-butoxy, pentoxy, 3-pentoxy, or hexyloxy; $(C_1-C_6)$alkanoyl can be acetyl, propanoyl or butanoyl; halo$(C_1-C_6)$alkyl can be iodomethyl, bromomethyl, chloromethyl, fluoromethyl, trifluoromethyl, trichloromethyl, 2-chloroethyl, 2-fluoroethyl, 2,2,2-trifluoroethyl, or pentafluoroethyl; hydroxy$(C_1-C_6)$alkyl can be hydroxymethyl, 1-hydroxyethyl, 2-hydroxyethyl, 1-hydroxypropyl, 2-hydroxypropyl, 3-hydroxypropyl, 1-hydroxybutyl, 4-hydroxybutyl, 1-hydroxypentyl, 5-hydroxypentyl, 1-hydroxyhexyl, or 6-hydroxyhexyl; $(C_1-C_6)$ alkoxycarbonyl can be methoxycarbonyl, ethoxycarbonyl, propoxycarbonyl, isopropoxycarbonyl, butoxycarbonyl, pentoxycarbonyl, or hexyloxycarbonyl; $(C_1-C_6)$alkylthio can be methylthio, ethylthio, propylthio, isopropylthio, butylthio, isobutylthio, pentylthio, or hexylthio; $(C_1-C_6)$ alkanoyloxy can be formyloxy, acetoxy, propanoyloxy, butanoyloxy, isobutanoyloxy, pentanoyloxy, or hexanoyloxy; aryl can be phenyl, indenyl, or naphthyl; and heteroaryl can be furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide) or quinolyl (or its N-oxide).

A specific value for $R_1$ is hydrogen. Another specific value for $R_1$ is halo (e.g. bromo).

A specific value for $R_2$ is phenyl, optionally substituted by 1, 2, or 3 substituents independently selected from the group consisting of $(C_1-C_6)$alkyl, $(C_1-C_6)$alkoxy, hydroxy, halo, nitro, cyano, mercapto, carboxy, halo$(C_1-C_6)$alkyl, trifluoromethoxy, $(C_1-C6)$alkanoyl, $(C_1-C_6)$alkoxycarbonyl, $(C_1-C_6)$alkylthio, and $(C_1-C_6)$alkanoyloxy. Another specific value for $R_2$ is phenyl.

A specific value for each of $R_3$, $R_4$, and $R_5$ is hydrogen.

A specific value for $R_6$ or $R_7$ is $(C_1-C_6)$alkoxy, hydroxy, halo, nitro, cyano, mercapto, carboxy, hydroxy$(C_1-C_6)$alkyl, halo$(C_1-C_6)$alkyl, trifluoromethoxy, $(C_1-C_6)$alkanoyl, $(C_1-C_6)$alkoxycarbonyl, $(C_1-C_6)$alkylthio, or $(C_1-C_6)$alkanoyloxy. Another specific value for each of $R_6$ and $R_7$ is hydrogen.

A specific value for $R_8$ is hydroxy, halo, nitro, cyano, mercapto, carboxy, $(C_1-C_6)$alkoxy, —$NR_aR_b$, halo$(C_1-C_6)$alkyl, trifluoromethoxy, $(C_1-C_6)$alkanoyl, $(C_1-C_6)$alkoxycarbonyl, $(C_1-C_6)$alkylthio, or $(C_1-C_6)$alkanoyloxy. Another specific value for $R_8$ is $(C_1-C_6)$alkyl substituted by 1, 2, or 3 substituents independently selected from the group consisting of hydroxy, nitro, cyano, mercapto, carboxy, $(C_1-C_6)$alkoxy, —$NR_aR_b$, trifluoromethoxy, $(C_1-C_6)$alkanoyl, $(C_1-C_6)$alkoxycarbonyL $(C_1-C_6)$alkylthio, and $(C_1-C_6)$alkanoyloxy. Another specific value for $R_8$ is $(C_1-C_6)$alkyl substituted by hydroxy, nitro, cyano, mercapto, carboxy, $(C_1-C_6)$alkoxy, —$NR_aR_b$, trifluoromethoxy, $(C_1-C_6)$alkanoyl, $(C_1-C_6)$alkoxycarbonyl, $(C_1-C_6)$alkylthio, or $(C_1-C_6)$alkanoyloxy.

A preferred value for $R_1$ is hydrogen; for $R_2$ is phenyl; and for $R_8$ is halo or trifluoromethyl. A more preferred value for $R_8$ is trifluoromethyl.

A preferred group of compounds of formula I wherein $R_1$ and $R_2$ are each halo (e.g. bromo).

Processes for preparing compounds of formula I are illustrated by the following procedures in which the meanings of the generic radicals are as given above unless otherwise qualified.

A compound of formula I wherein $R_8$ is hydroxy can be prepared by treating an intermediate of formula II:

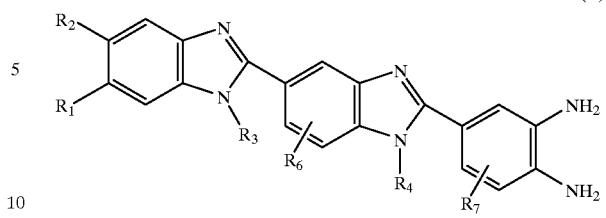

with urea, for example, using conditions similar to those described in Example 1.

A compound of formula I wherein $R_8$ is mercapto can be prepared by treating an intermediate of formula II with ethylxanthic acid potassium salt, for example, using conditions similar to those described in Example 2.

A compound of formula I wherein $R_8$ is amino can be prepared by treating an intermediate of formula II with cyanogen bromide, for example, using conditions similar to those described in Example 3.

Compounds of formula I can generically be prepared by reacting an intermediate diamine of formula III with an intermediate aldehyde of formula IV.

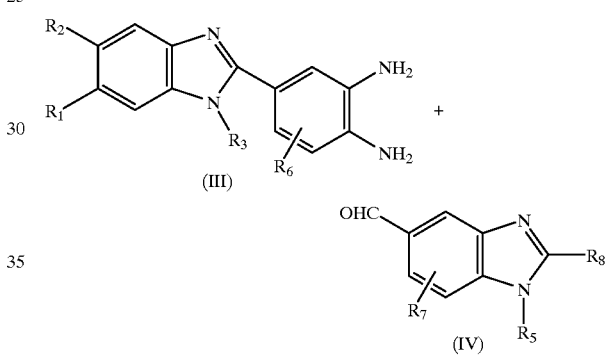

The reaction can conveniently be carried out under conditions similar to those described in the Examples (e.g., Example 4).

Compounds of formula I can also generally be prepared by reacting an intermediate diamine of formula V with an aldehyde of formula VI.

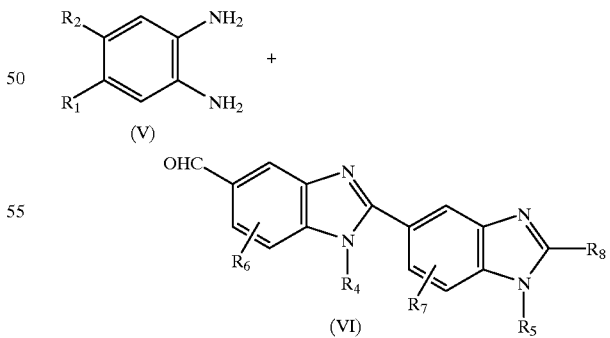

The reaction can conveniently be performed under conditions similar to those described in the Examples (e.g. Example 12).

Compounds of formula I comprising a hydroxy group can be prepared from a corresponding compound of formula I comprising a methoxy group by treatment with boron tribromide, for example using conditions similar to those described in Example 7.

Compounds of formula I comprising a amino group can be prepared from a corresponding compound of formula I comprising a acetamido group by hydrolysis using conditions similar to those described in Example 8.

Intermediates of formula II, III, IV, V, and VI wherein $R_1$-$R_8$ have any of the values, specific values, or preferred values defined herein for the corresponding radicals in a compound of formula I, are particularly useful for preparing compounds of formula I.

In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, $\alpha$-ketoglutarate, and $\alpha$-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example, calcium) salts of carboxylic acids can also be made.

The compounds of formula I can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thiomersal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compound(s) of formula I in a liquid composition, such as a lotion, will be from about 0.1–25 wt-%, preferably from about 0.5–10 wt-%. The concentration in a semi-solid or solid composition such as a gel or a powder will be about 0.1–5 wt-%, preferably about 0.5–2.5 wt-%.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The compound is conveniently administered in unit dosage form; for example, containing 5 to 1000 mg, conveniently 10 to 750 mg, most conveniently, 50 to 500 mg of active ingredient per unit dosage form.

Ideally, the active ingredient should be administered to achieve peak plasma concentrations of the active compound of from about 0.5 to about 75 $\mu$M, preferably, about 1 to 50 $\mu$M, most preferably, about 2 to about 30 $\mu$M. This may be achieved, for example, by the intravenous injection of a 0.05 to 5% solution of the active ingredient, optionally in saline, or orally administered as a bolus containing about 1–100 mg of the active ingredient. Desirable blood levels may be maintained by continuous infusion to provide about 0.01–5.0 mg/kg/hr or by intermittent infusions containing about 0.4–15 mg/kg of the active ingredient(s).

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The ability of a compound of the invention to effect topoisomerase I mediated DNA cleavage can be determined using pharmacological models that are well known to the art, for example, using a model like Test A described below.

Test A. Topoisomerase I Cleavage Assay.

Representative compounds of the invention were evaluated in a cleavage assay using recombinant topoisomerases I. This assay was preformed as described by B. Gatto et al. *Cancer Res.*, 1996, 56, 2795–2800. Human topoisomerase I was isolated as a recombinant fusion protein using a T7 expression system. Plasmid YEpG was purified by the alkali lysis method followed by phenol deproteination and CsCl/ethidium isopycnic centrifiigation as described by Maniatis, T.; Fritsch, E. F.; Sambrook, *J. Molecular Cloning, a Laboratory Manual;* Cold Spring Harbor Laboratory: Cold Spring Harbor, N.Y. 1982; pp 149–185. The end-labeling of the plasmid was accomplished by digestion with a restriction enzyme followed by end-filling with Klenow polymerase as previously described by Liu, L. F.; Rowe, T. C.; Yang, L.; Tewey, K. M.; Chen, G. L. "Cleavage of DNA by mammalian topoisomerase II," *J. Biol. Chem.* 1983, 258, 15365. $IC_{50}$ values were calculated after 4 days of continuous drug exposure. Topoisomerase I cleavage values are reported as REC, Relative Effective Concentration (i.e., concentrations relative to compound 5, whose value is arbitrarily assumed as 1) that is able to produce the same cleavage on the plasmid DNA in the presence of human topoisomerase I.

The cytotoxic effects of a compound of the invention can be determined using pharmacological models that are well known to the art, for example, using a model like Test B described below.

Test B. Cytotoxicity Assay.

Cytotoxicity was determined using the MTT-microtiter plate tetrazolinium cytotoxicity assay (MTA) (See Chen A. Y. et al. *Cancer Res.* 1993, 53, 1332; Mosmann, T. J., *J. Immunol. Methods* 1983, 65, 55; and Carmichael, J. et al. *Cancer Res.* 1987, 47, 936). The human lymphoblast RPMI 8402 and its camptothecin-resistant variant cell line, CPT-K5 were provided by Dr. Toshiwo Andoh (Aichi Cancer Center Research Institute, Nagoya, Japan) (see Andoh, T.; Okada, K. "Drug resistance mechanisms of topoisomerase I drugs," *Adv. in Pharmacology* 1994, 29B, 93. The cytotoxicity assay was performed using 96-well microtiter plates. Cells were grown in suspension at 37° C. in 5% $CO_2$ and maintained by regular passage in RPMI medium supplemented with 10% heat- inactivated fetal bovine serum, L-glutamine (2 mM), penicillin (100 U/mL), and streptomycin (0.1 mg/mL). For determination of $IC_{50}$, cells were exposed continuously with varying concentrations of drug and MTT assays were performed at the end of the fourth day.

Data from Test A and Test B is shown in FIG. 2 for representative compounds of the invention.

Compounds of formula I are potent topoisomerase I poisons. Additionally, compounds of formula I exhibit cytotoxic activity against RPMI 8402 cancer cells and camptothecin resistant CPT-K5 cells. Accordingly, compounds of formula I are useful as cytotoxic agents, for the treatment of cancers, and in particular, solid mammalian tumors or hematologic malignancies. Compounds of the invention are also useful as pharmacological tools for in vitro and in vivo study of topoisomerase function and activity.

As used herein, the term "solid mammalian tumors" includes cancers of the head and neck, lung, mesothelioma, mediastinum, esophagus, stomach, pancreas, hepatobiliary system, small intestine, colon, rectum, anus, kidney, ureter, bladder, prostate, urethra, penis, testis, gynecological organs, ovarian, breast, endocrine system, skin central nervous system; sarcomas of the soft tissue and bone; and melanoma of cutaneous and intraocular origin. The term "hematological malignancies" includes childhood leukemia and lymphomas, Hodgkin's disease, lymphomas of lymphocytic and cutaneous origin, acute and chronic leukemia, plasma cell neoplasm and cancers associated with AIDS. The preferred mammalian species for treatment are humans and domesticated animals.

The compounds are also expected to exhibit some of the other bioactivities observed for topoisomerase inhibitors, such as antibacterial, antifungal, antiprotozoal, antielmintic and/or antiviral activity. In particular, the compounds may exhibit antifungal activity. Thus, the invention also provides a therapeutic method to treat fungal infection comprising administering to a mammal afflicted with a fungal infection, an effective antifungal amount of a compound of the formula I, or a pharmaceutically acceptable salt thereof.

The invention will now be illustrated by the following non-limiting Examples, wherein unless otherwise stated: melting points were determined with a Thomas-Hoover Unimelt capillary melting point apparatus; column chromatography refers to flash chromatography conducted on SiliTech 32–63 μm, (ICN Biomedicals, Eschwegge, Ger.) using the solvent systems indicated; infrared spectral data (IR) were obtained on a Perkin-Elmer 1600 Fourier transform spectrophotometer and are reported in cm$^{-1}$; proton ($^1$H NMR) and carbon ($^{13}$C NMR) nuclear magnetic resonance were recorded on a Varian Gemini-200 Fourier Transform spectrometer; NMR spectra (200 MHZ $^1$H and 50 MHZ $^{13}$C) were recorded in the deuterated solvent indicated with chemical shifts reported in δ units downfield from tetramethylsilane (TMS); coupling constants are reported in hertz (Hz); mass spectra were obtained from Washington University Resource for Biomedical and Bio-organic Mass Spectrometry within the Department of Chemistry at Washington University, St. Louis, Mo.; and combustion analyses were performed by Atlantic Microlabs, Inc., Norcross, Ga., and were within ±0.4% of the theoretical value.

EXAMPLES

Example 1

5-Phenyl-2-[2'(2"-hydroxybenzimidazol-5"-yl) benzimidazol-5'-yl]benzimidazole (2).

5-Phenyl-2-[2'-(3,4-diaminophenyl)benzimidazol-5'yl] benzimidazole, (29.7 mg, 0.07 mmol) and urea (6 mg, 0.1 mmol) were dissolved in DMF (0.4 ml). The mixture was refluxed at 150° C. for 7 hours. The cooled reaction mixture when concentrated in vacuo and washed with water provided 27.6 mg (88%) of pure yellow solid; mp>280° C.; IR (KBr) 3382, 3133, 1693, 1475, 1444, 1279; $^1$H NMR (DMSO-d$_6$ +3 drops CF$_3$COOH) δ 7.3 (d,1H,J=8.14), 7.46–7.80 (m,3H), 7.80 (d,2H,J=8.1), 7.89–8.01(m,4H), 8.05–8.14 (m,2H), 8.32 (d,1H,J=8.34), 8.63 (s,1H), 11.35 (s,1H); $^{13}$C NMR (DMSO-d$_6$+3 drops CF$_3$COOH) δ 108.07, 109.55, 111.78, 114.03, 114.57, 114.62, 115.3, 120.21, 122.53, 125.45, 125.82, 127.42, 128.1, 129.26, 130.81, 131.59, 132.66, 132.87, 135.15, 135.33, 139.20, 139.61, 149.32, 153.14, 155.71; HRMS (FAB) calculated for C$_{27}$H$_{19}$N$_6$(MH$^+$) 443.1620 found 443.1625.

The intermediate 5-phenyl-2-[2'-(3,4-diaminophenyl) benzimidazol-5'yl]benzimidazole was prepared as follows.
a. 5-Phenyl-2-[2'-(3,4diaminophenyl)benzimidazol-5'-yl] benzimidazole. A solution of 5-phenyl-2-[2'-(3,4-dinitrophenyl)benzimidazol-5'yl]benzimidazole (75 mg, 0.16 mmol) in ethyl acetate (50 mL) was reduced by hydrogenation over 10% Pd/C (15 mg) for 90 minutes. The resulting solution was passed through a bed of Celite and the ethyl acetate was removed to give the diamine, which was used without further purification.

The starting 5-phenyl-2-[2'-(3,4-dinitrophenyl) benzimidazol-5'yl]benzimidazole can be prepared as described by J. S. Kim et al. J. Med. Chem. 1997, 40, 2818–2824.

Example 2

5-Phenyl-2-[2'-(2"-mercaptobenzimidazol-5"-yl) benzimidazol-5'-yl]benzimidazole (3).

5-Phenyl-2-[2'-(3,4-diaminophenyl)benzimidazol-5'yl] benzimidazole, (59.4 mg, 0.14 mmol) and ethylxanthic acid potassium salt (25.1 mg, 0.16 mmol) were refluxed in ethanol (1 ml) and distilled water (0.1 ml) overnight. The cooled reaction mixture was acidified to pH 3 with glacial acetic acid, volume condensed in vacuo and purified directly by column chromatography. Elution with (40–100%) ethyl acetate/n-hexanes provided 69% of yellow solid; mp>280° C.; IR (KBr) 3089, 2926, 2851, 1712, 1624, 1549, 1449, 1380, 1274, 1186, 1079; $^1$H NMR (DMSO-d$_6$+3 drops CF$_3$COOH) δ 7.33–7.42 (m,2H), 7.48–7.63 (t,4H), 7.71–7.82 (m,4H), 7.89 (s,1H), 8.04–8.06 (m,1H), 8.1–8.24 (m,1H), 8.42 (d,1H,J=2.4); $^{13}$C NMR (DMSO-d$_6$+3 drops CF$_3$COOH) δ 107.37, 107.15, 109.2, 109.68, 111.81, 111.73, 113.31, 113.53, 114.57, 114.64, 114.68, 115.56, 125.26, 127.44, 128.16, 129.33, 131.64, 132.93, 133.27, 139.1, 136.61, 139.62, 149.51, 152.94, 171.13; HRMS (FAB) calculated for C$_{27}$H$_{19}$N$_6$S (MH$^+$) 459.1392, found 459.1403.

Example 3

5-Phenyl-2-[2'-(2"-aminobenzimidazol-5"-yl) benzimidazol-5'-yl]benzimidazole (4).

5-Phenyl-2-[2'-(3,4-diaminophenyl)benzimidazol-5'yl] benzimidazole, (66 mg, 0.16 mmol) was dissolved in DMF (0.2 ml) and methanol (1 ml), and was added to cyanogen bromide (10% solution in water, 0.33 ml, 0.63 mmol). The reaction mixture was stirred overnight at room temperature. The mixture was concentrated under reduced pressure. Compound was recrystallized from methanol to give 47% of pale brown solid; mp>280° C.; IR (KBr) 3352, 3052, 2926, 1680, 1624, 1574, 1461, 1261,679; $^1$H NMR (DMSO-d$_6$+3 drops CF$_3$COOH) δ 7.46–7.62 (m,3H), 7.79 (d,2H,J=7.26), 7.87–7.96 (m,2H), 7.99–8.01 (m,2H), 8.20–8.26 (m,2H), 8.31 (s,1H), 8.72 (d,2H,J=9.12); $^{13}$C NMR (DMSO-d$_6$+3 drops CF$_3$COOH) δ 107.38, 110.89, 111.75, 111.78, 114.67, 115.13, 115.24, 115.92, 123.59, 125.58, 126.84, 127.5, 127.53, 127.57, 127.76, 128.2, 129.43, 130.86, 131.87, 133.13, 138.74, 139.74, 150.10, 152.14, 153.42; HRMS (FAB) calculated for C$_{27}$H$_{20}$N$_7$ (MH$^+$) 442.1780 found 442.1776.

Example 4

5-Phenyl-2-[2'(2"-trifluoromethylbenzimidazol-5"yl) benzimidazol-5'-yl]benzimidazole (5).

5-Phenyl-2-[3,4-diaminophenyl]benzimidazole (0.160 g, 0.53 mmol) was heated with 5-formyl-2-trifluoromethylbenzimidazole (0.12 g, 0.54 mmol) in nitrobenzene (4 mL) at 145° C. overnight. Nitrobenzene was removed using a Kugelrohr and the compound purified by column chromatography. (1–16%) methanol/ethyl acetate provided 40% pure yellow compound; mp>280° C.; IR (KBr) 3047, 2927, 1698, 1626, 1543, 1440, 1287, 1158; $^1$H NMR (DMSO-d$_6$+3 drops CF$_3$COOH)δ 7.44–7.59 (m,3H), 7.79 (d,2H,J=7.04), 7.87–8.01 (m,2H), 8.05–8.09 (m,2H), 8.15–8.19 (m,1H), 8.29–8.35 (m,2H), 8.70 (m,2H); $^{13}$C NMR (DMSO-d$_6$+3 drops CF$_3$COOH) δ 111.79, 114.68, 114.92, 115.85, 117.53, 117.58, 118.37, 118.41, 119.58, 120.46, 124.14, 124.79, 125.71, 125.74, 127.47, 128.18, 129.36, 131.73, 132.99, 134.93, 137.44, 138.97, 139.02, 139.07, 139.66, 140.34, 149.81, 153.46; HRMS (FAB) calculated for C$_{28}$H$_{18}$N$_6$F$_3$ (MH$^+$) 495.1545 found 495.1543.

The intennediate 5-formyl-2-trifluoromethylbenzimidazole was prepared as follows.
a. 3,4-Diaminobenzonitrile. 4-Amino-3-nitrobenzonitrile (3 g, 18.4 mmol) in ethyl acetate (120 ml) was reduced by hydrogenation using 45 psi of $H_2$ and 10% Pd-C (300 mg) for 1.5 hr. After passing through a bed of celite, the solvent was removed in vacuo and 2.43 g (99%) of white solid was obtained; mp 144–145° C.; IR (KBr) 3431, 2726, 2211, 1861, 1631, 1311, 1149, 722; $^1$H NMR (CDCl$_3$) δ 3.18–3.87 (brs, 4H),6.68 (d, 1H, J=8.06), 6.94 (d,1H,J=1.74), 7.02–7.27 (dd,1H,J=1.78, 8.06); $^{13}$C NMR (CDCl$_3$) δ 100.27, 115.86, 119.52, 122.19, 125.66, 135.94, 142.52; The crude diamine obtained was typically used without further purification.

b. 5-Cyano-2-trifluoromethylbenzimidazole. 3,4 Diaminobenzonitrile (200 mg, 1.5 mmol) was refluxed with trifluoroacetic acid (0.3 ml) for 6 hours. The mixture was neutralized with 2 N NaOH and extracted with ethyl acetate. The ethyl acetate layer was dried over anhydrous Na$_2$SO$_4$. Column with (0–10%) ethyl acetate/n-hexanes gave 88% of pure white compound; mp 182–183° C.; $^1$H NMR (DMSO-d$_6$+3 drops CF$_3$COOH) δ 7.72–7.77 (1H,dd,J=1.46,8.56), 7.88 (d,1H, 8.42), 8.35 (s,1H); $^{13}$C NMR (DMSO-d$_6$+3 drops CF$_3$COOH) δ 106.47, 106.64, 112.36, 117.31, 118.09, 119.44, 123.53, 123.81, 127.47; Anal. calculated for C$_9$H$_4$N$_3$F$_3$: C; 51.20, H; 1.91, N; 19.90, found C; 51.45, H; 2.03, N; 19.68.

c. 5-Formyl-2-trifluoromethylbenzimidazole. 5-Cyano-2-trifluoromethyl-benzimidazole (196 mg, 0.93 mmol) was refluxed with HCOOH (14 ml), H$_2$O (5 ml) and Ni-Al (0.9 g) catalyst for 6 hours. The hot reaction mixture was filtered through celite and concentrated in vacuo. The solution was basified with 2N NaOH. Extraction with ethyl acetate followed by drying over anhydrous sodium sulfate and concentration of the ethyl acetate layer in vacuo gave the crude aldehyde. Purification was achieved by column chromatography. Elution with 10/90 ethyl acetate/n-hexanes gave 41% of pure white compound; mp 178–179° C.; IR (KBr) 3210, 2737, 1699, 1552, 1328, 1187 (d), 986; $^1$H NMR (DMSO-d$_6$+3 drops CF$_3$COOH) δ 7.87–7.95 (m, 2H), 8.34(s,1H), 10.11 (s,1H).$^{13}$C NMR (DMSO-d$_6$+3 drops CF$_3$COOH) δ 106.63, 112.35, 116.72, 118.08, 121.87, 123.80, 124.04, 132.95, 192.65; HRMS (EI) calculated for C$_9$H$_5$N$_2$OF$_3$ m/z 214.0354 found 214.0348.

The intermediate 4-amino-3-nitrobenzonitrile used in subpart a above is commercially available (Aldrich Chemical Company)

The intermediate 5-phenyl-2-[3,4-diaminophenyl] benzimidazole was prepared as follows.

d. 5-Phenyl-2-[3,4-diaminophenyl]benzimnidazole. 5-Phenyl-2-[3,4-nitrophenyl]benzimidazole (580 mg, 1.6 mmol) was dissolved in 100 ml ethyl acetate and hydrogenation was carried out using 10% Pd/C (100 mg) for 1.5 hours. The reaction mixture was passed through a bed of celite and the bed washed with methanol. The washings were concentrated in vacuo to yield (477 mg, 1.59 mmol) of the crude diamine in 98% yield. The diamine was not characterized but used without purification; $^1$H NMR (DMSO-d$_6$+3 drops CF$_3$COOH) δ 4.70 (brs,2H), 4.96 (brs, 2H), 6.62 (d,1H, 8.02), 7.37 (m,8H), 7.53 (m,2H).

Example 5

5-Phenyl-2-[2'-(2"-hydroxymethylbenzimidazol-5"-yl)benzimidazol-5'-yl]benzimidazole (7).

5-Phenyl-2-[3,4-diaminophenyl]benzimidazole (178 mg, 0.6 mmol) and 5-formyl-2-hydroxymethyl benzimidazole (104.2 mg, 0.6 mmol) were condensed in nitrobenzene (10 ml) overnight at 145° C. Nitrobenzene was removed from the reaction mixture with a Kugelrohr and the compound was purified directly by column chromatography. Elution with (1–18%) methanol/ethyl acetate provided 62% of yellow solid; mp>280° C.; IR (Nujol) 3406, 2922, 2725, 1631, 1553, 1461, 1377; $^1$H NMR (DMSO-d$_6$+3 drops CF$_3$COOH) δ 5.1 (s,2H), 7.45–7.59 (m,3H), 7.79 (d,2H,J= 6.96), 8.23–8.28 (m,1H), 8.47 (d,1H, J=8.59), 8.68 (s,2H); $^{13}$C NMR (DMSO-d$_6$+3 drops CF$_3$COOH) δ 55.80, 111.69, 113.68, 114.59, 115.32, 115.77, 116.21, 118.31, 123.77, 124.52, 125.21, 125.61, 127.47, 127.49, 127.54, 128.14, 129.38, 131.64, 131.89, 132.91, 133.54, 137.66, 138.86, 139.68, 140.13, 150.25, 153.37, 157.62; HRMS (FAB) calculated for C$_{28}$H$_{21}$N$_6$O (MH$^+$) 457.1777 found 457.1774.

The intermediate 5-formyl-2-hydroxymethyl benzimidazole was prepared as follows.

a. 5-Cyano-2-hydroxymethylbenzimidazole. 3,4 Diaminobenzonitrile (0.2 g, 1.50 mmol) was heated with glycolic acid (0.18 g, 2.37 mmol) in HCl (1.5 ml of 4N) for 2 hours. After neutralization with 2M sodium carbonate the product was extracted into ethyl acetate, dried over anhydrous Na$_2$SO$_4$ and concentrated in vacuo to give a white colored solid. The compound was purified by column chromatography. Elution with (75–100%) ethyl acetate/n-hexanes gave 65.5% (133 mg, 0.76 mmol) of pure compound; mp 172–173° C.; IR (Nujol) 3350, 2928, 2219, 1621, 1536, 1302, 1217, 1036, 815; $^1$H NMR (DMSO-d$_6$+3 drops CF$_3$COOH) δ 4.88 (s,2H), 7.52–7.57 (dd,1H,J=1.46,8.38), 7.69 (d,1H,J=8.36), 7.95 (s,1H), $^{13}$C NMR (DMSO-d$_6$+3 drops CF$_3$COOH) δ 55.81, 107.99, 115.68, 118.64, 119.50, 129.00, 131.50, 134.39; HRMS (EI) calculated for C$_9$H$_7$N$_3$O (m/z) 173.0590 found 173.0590.

b. 5-Formyl-2-hydroxymethylbenzimidazole. Ni-Al (1.2 g) was added to a solution of 5-cyano-2-hydroxymethylbenzimidazole (0.17 g, 0.97 mmol) in HCOOH (17 ml) and water (1.6 ml). The reaction mixture was heated at 95° C. for 5 hours. The hot mixture was filtered through a bed of celite and the reaction flask and the celite bed rinsed with water and then methanol. The combined solution was concentrated in vacuo. After addition of water to this residue, a white precipitate was formed. The pH of this suspension was adjusted to 9 by dropwise addition of 2N NaOH. The product was obtained by extraction with ethyl acetate. The ethyl acetate extract was dried over anhydrous Na$_2$SO$_4$ and concentrated in vacuo to give a pure white product (61% yield); mp 189–190° C.; IR (KBr) 3309, 2924, 1674, 1619, 1434, 1291, 1073, 808; $^1$H NMR (DMSO-d$_6$+3 drops CF$_3$COOH) δ 5.07 (s,2H), 7.94 (d,1H,J=8.68), 8.04–8.09 (dd,1H,J=1.34, 8.51), 8.32 (s,1H), 10.4 (s,1H); $^{13}$C NMR (DMSO-d$_6$+3 drops CF$_3$COOH) δ 55.76, 114.95, 116.81, 126.03, 131.45, 133.89, 135.11, 192.31; HRMS (EI) calculated for C$_9$H$_8$N$_2$O m/z 176.0586 found 176.0586.

Example 6

5-Phenyl-2-[2'-[2"-[2-(N-benzoyl)aminomethyl] benzimidazol-5"-yl]benzimidazol-5'-yl] benzimidazole (8).

5-Phenyl-2-[3,4-diaminophenyl]benzimidazole (75 mg, 0.25 mmol) and 5-formyl-2-[(N-benzoyl)aminomethyl] benzimidazole (70 mg, 0.25 mmol,) were heated in nitrobenzene (6 ml) at 145° C. overnight. Nitrobenzene was removed with a Kugelrohr and the compound was loaded on a column. (2–20%) methanol/ethyl acetate gave 45% yellowish compound; mp>280° C.; IR (KBr) 3204, 1637, 1542, 1442, 1384, 1292, 1026, 818; $^1$H NMR (DMSO-d$_6$+3 drops CF$_3$COOH) δ 7.46–7.66 (m,6H), 7.80 (d, 2H, J=7.06), 7.87–8.1 (m, 7H), 8.21–8.25 (m,1H), 8.43–8.48 (m,1H), 8.67 (s,2H); $^{13}$C NMR (DMSO-d$_6$+3 drops CF$_3$COOH) δ 36.65, 107.37, 111.73, 114.53, 114.58, 115.26, 115.49, 116.01, 119.47, 122.49, 124.81, 125.56, 126.72, 127.41, 127.83, 128.04, 128.07, 128.54, 129.25, 131.56, 131.87, 132.12, 132.84, 133.17, 134.11, 136.21, 137.76, 139.08, 139.66, 149.67, 152.62, 155.64, 167.60; HRMS (FAB) calculated for C$_{35}$H$_{26}$N$_7$O (MH$^+$) 560.2199 found 560.2209.

The intermediate 5-formyl-2-[(N-benzoyl)aminomethyl]benzimidazole was prepared as follows.

a. 5-Cyano-2-[(N-benzoyl)aminomethyl]benzimidazole. 3,4-Diaminobenzonitrile (250 mg, 1.88 mmol) was finely ground in a mortar with (0.34 g, 1.9 mmol) hippuric acid and intimately mixed and then carefully fused for 3 hours. The temperature was then raised to 160° C. when water was evolved as bubbles. After cooling the glassy mass was dissolved in ethyl acetate and purified by column chromatography. (50–100%) ethyl acetate/n-hexanes yielded 86% of pale buff colored compound; mp 131–132° C.; IR (Nujol) 2826, 2221, 1635, 1313, 1019, 814; $^1$H NMR (DMSO-d$_6$+3 drops CF$_3$COOH) δ 4.97 (d,2H,J=5.22), 7.52–7.61 (m,3H), 7.91–7.99 (m,4H), 8.37 (s,1H); $^{13}$C NMR (DMSO-d$_6$+3 drops CF$_3$COOH) δ 36.80, 107.73, 115.72, 118.81, 119.67127.83, 128.61, 128.64, 128.67, 128.78, 132.15, 132.20, 13322, 135.01, 156.13, 167.51; HRMS (EI) calculated for C$_{16}$H$_{12}$N$_4$O m/z 276.1011 found 276.1012.

b. 5-Formyl-2-[(N-benzoyl)aminomethyl]benzimidazole. 5-Cyano-2-[(N-benzoyl)aminomethyl]benzimidazole (0.33 g, 1.2 mmol) was dissolved in formic acid (18 ml). Water (5 ml) and Ni-Al (1.14 g) were added to it. The mixture was heated under nitrogen at 95° C. for 6 hours and while hot passed through a celite bed. The bed was washed with methanol and the washings concentrated in vacuo. The pH of the solution was adjusted with 2N NaOH to 9.0 and extracted with ethyl acetate. The extractions were dried over anhydrous Na$_2$SO$_4$ and concentrated in vacuo. The residue was purified over column chromatography using (50–100%) ethyl acetate/n-hexanes to give 26% of pure cream colored product; mp 108–109° C.; IR (KBr) 3314, 2933, 1687, 1646, 1539, 1289, 806; $^1$H NMR (DMSO-d$_6$+3 drops CF$_3$COOH) δ 4.99 (d,1H,J=5.12), 7.54–7.63 (m,4H), 7.93–8.07 (m,3H), 8.34 (s,1H), 10.15 (s,1H); $^{13}$C NMR (DMSO-d$_6$+3 drops CF$_3$COOH) δ 36.83, 115.10, 117.18, 125.80, 127.85, 128.71, 132.26, 132.33, 133.2, 133.68, 155.77, 167.54, 192.54; HRMS (EI) calculated for C$_{16}$H$_{13}$N$_3$O$_2$ m/z 279.1008 found 279.1003.

Example 7

5-Phenyl-2-[2'-[2"-(2-hydroxyethyl)benzimidazol-5"-yl]benzimidazol-5'-yl]benzimidazole (10)

5-Phenyl-2-[2'-[2"-(2-methoxyethyl)benzimidazol-5"-yl]benzimidazol-5'-yl]benzimidazole (30 mg, 0.06 mmol, Example 10) was suspended in freshly distilled ethyl acetate (30 ml) to which was added 10 equivalence of BBr$_3$ (0.62 ml, 1.0M) at −78° C. After stirring at room temperature overnight, the reaction was quenched by adding water (10 ml). The mixture was basified to pH 9.0 with ammonium hydroxide and extracted with ethyl acetate and dried over anhydrous Na$_2$SO$_4$. The crude mixture was separated on a chromatotron, (0–30%) methanol/ethyl acetate to give 10.6 mg of the product in 33% yield as a brown solid. mp>280° C.; IR (KBr) 3401, 3150, 2876, 1632, 1540, 1442, 1388, 1268, 1013, 823; $^1$H NMR (DMSO-d$_6$+3 drops CF$_3$COOH) δ 3.35 (t,2H), 3.98 (t,2H), 7.42–7.56 (m,3H), 7.76 (d,2H,J=7.7), 7.85–7.98 (m,2H), 8.06–8.19 (m,3H), 8.33 (d,1H, J=8.5), 8.44 (d,1H, J=8.8), 8.73 (s,2H); $^{13}$C NMR (DMSO-d$_6$+3 drops CF$_3$COOH) δ 30.75, 58.09, 111.71, 114.36, 114.53, 115.28, 115.98, 116.02, 118.28,119.43, 122.37, 124.71, 124.76, 125.43, 125.73, 127.40, 128.1, 129.25, 131.55, 131.64, 132.83, 133.95, 135.26, 137.79, 139.06, 139.64, 149.67, 152.63, 156.21; HRMS (FAB) calculated for C$_{29}$H$_{23}$N$_6$O (MH$^+$) 471.1933 found 471.1935.

Example 8

5-Phenyl-2-[2'-[2"-(2-aminoethyl)benzimidazol-5"-yl]benzimidazol-5'-yl]benzimidazole (11)

5-Phenyl-2-[2'-[2"-(2-acetamidoethyl)benzinidazol-5"-yl)]benzimidazol-5'-yl]benzimidazole (35 mg, 0.07 mmuyol, Example 9) was hydrolyzed with 2N HCl (5 ml) at 110° C. for 3 hours. The cooled reaction mixture was basified with arnmonium hydroxide to pH 9.0 and purified by column chromatography. Elution with 50:50 methanol/ethyl acetate provided 75% yellow solid; mp>280° C.; IR (Nujol) 3375, 2719, 1553, 1461,1377; $^1$H NMR (DMSO-d$_6$+3 drops CF$_3$COOH) δ 3.45–3.52 (m,4H), 7.45–7.56 (m,2H), 7.79(d, 2H, J=7.04), 7.88–8.00 (m,2H), 8.07–8.27 (m,5H),8.42 (d,1H, J=8.92), 8.68 (d,2H,J=4.76); $^{13}$C NMR (DMSO-d$_6$+3 drops CF$_3$COOH) δ 25.52, 36.36, 111.74, 113.77, 114.62, 115.33, 115.76, 116.17, 118.33, 123.75, 123.94, 124.75, 125.61, 127.48, 128.16, 129.39, 131.71, 132.98, 133.11, 134.77, 137.73, 138.84, 139.71, 140.12, 150.34, 153.43, 153.61; HRMS (FAB) calculated for C$_{27}$H$_{19}$N$_6$O (MH$^+$) 470.2093 found 470.2089.

Example 9

5Phenyl-2-[2'-(2"(2-acetamidoethyl)benzimidazol-5"-yl)]benzimidazol-5'-yl] benzimidazole (12).

5-Phenyl-2-[3,4-diaminophenyl]benzimidazole (124 mg, 0.41 mmol) and 5-formyl-2-(2-acetamidoethyl)benzimidazole (95 mg, 0.41 mmol) were condensed in nitrobenzene (7 ml) overnight at 145° C. Nitrobenzene was removed with the aid of a Kugelrohr and the compound purified directly by flash column chromatography. Elution with (1–15 %) methanol/ethyl acetate provided 69% of yellow solid; mp>280° C.; IR (KBr) 3064, 2954, 2862, 1654, 1556, 1442, 1286; $^1$H NMR (DMSO-d$_6$+3 drops CF$_3$COOH) δ 1.81 (s,3H), 3.18–3.35 (m,2H), 3.61–3.64 (m,2H), 7.45–7.6 (m,3H), 7.79 (d,2H,J=7.04 ), 7.87–8.00 (m,2H), 8.07–8.30 (m,4H), 8.46 (d,1H,J=8.5), 8.71 (s,2H); $^{13}$C NMR (DMSO-d$_6$3 drops CF$_3$COOH) δ 22.59, 27.89, 36.41, 111.73, 113.66, 114.59, 115.22, 115.69, 116.17, 118.61, 124.04, 125.22, 125.66, 127.47, 127.56, 128.14, 128.18, 129.36, 131.62, 131.84, 132.89, 133.69, 137.10, 138.94, 139.54, 139.68, 150.16, 153.24, 155.40, 158.47, 170.27; HRMS (FAB) calculated for C$_{31}$H$_{25}$N$_7$O (MH$^+$) 512.2199 found 512.2201.

The intermediate 5-formyl-2-(2-acetamidoethyl) benzimidazole was prepared as follows.

a. 5-Cyano-2-(2-aminoethyl)benzimidazole. A solution of 3,4 diaminobenzonitrile (1 g, 7.52 mmol) and β-alanine (1.0 g, 11.3 mmol) in HCl (8 ml, 6N) was refluxed for 24 hrs. At this time the diamine was barely detectable by TLC. After neutralization with 2N NaOH, the compound was directly loaded on the column. Elution with (75–100%) ethyl acetate/n-hexanes and further with (1–25%) methanol/ethyl acetate gave 46% (0.65 g) of pure yellow compound; mp 105–106° C.; IR (KBr) 3438, 2855, 2734, 2212, 1625, 1569, 1483, 1457, 1385, 1222, 1153; $^1$H NMR (CD$_3$OD) δ 3.09–3.13 (m,4H), 7.49–7.66 (m,2H), 7.91 (d,1H,J=1.46); $^{13}$C NMR (CD$_3$OD) δ 33.13, 40.99, 106.27, 116.57, 121.04, 121.19, 127.08, 140.40, 142.59, 158.82; HRMS (EI) calculated for C$_{10}$H$_{10}$N$_4$ m/z 186.0905 found 186.0906.

b. 5-Cyano-2-(2-acetamidoethyl)benzimidazole. 5-Cyano-2-(2-aminoethyl)benzimidazole (0.4 g, 2.15 mmol) was refluxed in dry THF (10 ml), acetic anhydride (0.4 ml) and triethylamine (0.4 ml) for 4 hrs. The mixture was neutralized with 2N NaOH and extracted with ethyl acetate to give the crude acetamide. The acetamide was purified using flash column chromatography. Elution with (0–15%) methanol/ethyl acetate gave 70% of pure white compound; mp 218–219° C.; IR (KBr) 3233, 3053, 2225, 1653, 1573, 1442, 1374, 1303, 1058, 815; $^1$H NMR (DMSO-d$_6$+3 drops CF$_3$COOH) δ 1.78 (s,3H), 3.26 (t,2H), 3.53–3.62 (2H, J=6.45, 12.38), 7.89–7.95 (dd, 1H, J=1.42, 8.48), 8.00 (d, J=8.22,1H), 8.19 (t,1H), 8.45 (d,1H,J=1.42); $^{13}$C NMR (DMSO-d$_6$+3 drops CF$_3$COOH) δ 22.57, 27.82, 36.71, 108.06, 115.52, 118.62, 119.33, 129.02, 131.29, 134.26, 156.23, 170.18; Anal. calculated for C$_{12}$H$_{12}$N$_4$O.¼H2O: C; 61.92, H; 5.41, N; 24.07 found C; 62.60, H; 5.41, N; 23.82.

c. 5-Formyl-2-(2-acetamidoethyl)benzimidazole. 5-Cyano-2-(2-acetamidoethyl)benzimidazole (94.6 mg, 0.41 mmol) was refluxed in HCOOH (5.9 ml), water (0.5 ml) and Ni-Al (0.4 g) catalyst for six hours. The mixture was filtered hot through celite and the bed washed with methanol. The washings were concentrated in vacuo. The concentrate was basified with 2N NaOH to pH 9 and extracted with ethyl acetate. The ethyl acetate layer was dried over anhydrous Na$_2$SO$_4$ and purified by flash column chromatography. (0–15%) methanol/ethyl acetate gave 80% (70.10 mg) of pure white product; mp 220–221° C.; IR (KBr) 3222, 3047, 1656, 1575, 1439, 1289, 1110, 1058, 816; $^1$H NMR (DMSO-d$_6$+3 drops CF$_3$COOH) δ 1.79 (s,3H), 3.29 (t, 2H), 3.54–3.64 (q, J=6.66, 12.64, 2H), 7.97–8.09 (m,2H), 8.19 (t,1H), 8.38 (s, 1H), 10.17 (s,1H); $^{13}$C (DMSO-d$_6$+3 drops CF$_3$COOH) δ 22.69, 27.91, 36.75, 114.89, 116.86, 125.84, 131.67, 133.81, 135.33, 155.88, 170.13, 192.47; Anal. calculated for C$_{12}$H$_{13}$N$_3$O: C; 62.32, H; 5.67, N; 18.17 found C; 62.10, H; 5.7, N; 17.92.

Example 10

5-Phenyl-2-[2'-[2"-(2-methoxyethyl)benzimidazol-5"-yl]benzimidazol-5'-yl]benzimidazole (13)

5-Phenyl-2-[3,4-diaminophenyl]benzimidazole (0.17 mg, 0.58 mmol) and 5-formyl-2-(2-methoxyethyl) benzimidazole (120 mg, 0.59 mmol) were heated together in of nitrobenzene (5 ml) for 15 hours at 145° C. Nitrobenzene was removed with a Kugelrohr and the compound was loaded onto a column. (1–12%) methanol/ethyl acetate gave 80% pure yellowish product; mp>280° C.; IR (KBr) 3157, 2933, 1629, 1551, 1441, 1385, 1288, 1108, 818, 760, 698;

$^1$H NMR (DMSO-d$_6$+3drops CF$_3$COOH) δ 3.33 (s,3H), 3.45 (t,2H), 3.89 (t,2H), 7.45–7.59 (m,3H), 7.79 (d,2H,J=7.04), 7.86–7.99 (m,2H), 8.06–8.14 (m,3H), 8.26–8.31 (dd, 1H, J=1.34, 8.4), 8.44–8.49 (dd,1H,J=1.02,8.82), 8.72 (s,2H); $^{13}$C NMR (DMSO-d$_6$+3 drops CF$_3$COOH) δ 27.71, 58.30, 68.17, 111.7, 113.69, 114.57, 115.22, 115.72, 116.19, 118.51, 123.94, 124.21, 125.26, 125.61, 127.46, 128.14, 129.36, 131.65, 131.71, 132.91, 133.49, 137.24, 138.72, 139.68, 150.15, 153.24, 155.27; HRMS (FAB) calculated for C$_{30}$H$_{25}$N$_6$O (MH$^+$) 485.2089 found 485.2089.

The intermediate 5-formyl-2-(2-methoxyethyl) benzimidazole was prepared as follows.

a. 5-Cyano-2(2-methoxyethyl)benzimidazole. 3,4-Diaminobenzonitrile (0.2 g, 1.5 mmol) was refluxed with (0.22 ml, 2.25 mmol) of 2-methoxypropionic acid in 4N HCl (2.5 ml) for 7 hours. After neutralization with 2N NaOH the mixture was extracted with ethyl acetate and dried over anhydrous Na$_2$SO$_4$ and concentrated in vacuo. The product was purified on column chromatography using (7–100%) ethyl acetate/n-hexanes to give a 50% yield of pure white product; mp 122–123° C.; IR (KBr) 2875, 2225, 1624, 1544, 1454, 1288, 1215, 1106, 824; $^1$H NMR (DMSO-d$_6$+3 drops CF$_3$COOH) δ 3.29 (s,3H), 3.42 (t,2H), 3.84 (t,2H), 7.87–8.00 (m,2H), 8.40 (s,1H); $^{13}$C NMR (DMSO-d$_6$+3 drops CF$_3$COOH) δ 27.65, 58.18, 68.02, 106.79, 115.56, 118.28, 119.37, 128.95, 131.31, 134.26, 156.12; Anal. calculated for C$_{11}$H$_{11}$N$_3$.½ H$_2$O: C; 62.84, H; 5.75, N; 19.97 found C; 62.71, H; 5.70, N; 18.83.

b. 5-Formyl-2-(2'-methoxyethyl)benzimidazole. 5-Cyano-2-(2-methoxyethyl)benzimidazole (0.12 g, 0.61 mmol) was mixed in HCOOH (9 ml) and water (1 ml), to which was added Ni-Al (0.6 g). The mixture was heated at 95° C. for 5.5 hours. The mixture was passed through a celite bed while hot and the bed was washed with methanol and the filtrate concentrated. After neutralization with 2N NaOH and extraction with CHCl$_3$, the extracts were dried over anhydrous Na$_2$SO$_4$ and concentrated in vacuo. The residue was purified by column chromatography using a gradient of 15–100% ethyl acetateln-hexanes to give a white product in 65% yield; mp 83–84° C.; IR (Nujol) 2846, 2728, 1692, 1290, 1109,816; $^1$H NMR (DMSO-d$_6$+3 drops CF$_3$COOH) δ 3.31(s,3H), 3.44 (t,2H), 3.86 (t,2H), 7.79–8.09 (m,2H), 8.36 (s,1H), 10.16 (s,1H); $^{13}$C NMR (DMSO-d$_6$+3 drops CF$_3$COOH) δ 27.73, 58.28, 68.08, 114.92, 116.86, 125.92, 131.55, 133.85, 135.19, 155.8, 192.43; Anal. calculated for C$_{11}$H$_{12}$N$_2$O$_2$¼ H$_2$O: C; 64.69, H; 5.92, N; 13.71 found C; 64.76, H; 6.02, N; 13.60.

Example 11

5-Bromo-2-[2'-[2"-hydroxybenzimidazol-5"-yl] benzimidazol-5'-yl]benzimidazole (18).

5-Bromo-2-[3,4-diaminophenyl]benzimidazole (33.3 mg, 0.11 mmol) and 5-formyl-2-hydroxybenzimidazole (17.7 mg, 0.11 mmol) were heated at 145° C. in nitrobenzene (3 ml) overnight. Nitrobenzene was removed with a Kugelrohr and the compound was purified by flash column chromatography. Elution with (5–15%) methanol/ethyl acetate gave 23.5 mg (0.05 mmol) of yellow colored compound in 48% yield; mp>280° C.; IR (KBr) 3409, 3211, 1698, 1558, 1482, 1384, 1279; $^1$H NMR (DMSO-d$_6$+3 drops CF$_3$COOH) δ 7.30 (d,1H,J=8.34), 7.69 (dd,1H, J=1.80, 8.71), 7.82 (s,1H), 7.86–7.99 (m,2H), 8.09–8.13 (m,2H), 8.32 (dd,1H,J=1.36, 8.69), 8.61 (s,1H), 11.38 (s, 1H); $^{13}$C (DMSO-d$_6$+3 drops CF$_3$COOH) δ 108.01, 10.55, 113.92, 115.16, 115.27, 116.25, 117.19, 117.86, 121.06, 122.41, 125.24, 128.70, 130.78, 132.66, 133.16, 134.85, 134.89, 135.62, 150.42, 153.09, 155.69; HRMS (FAB) calculated for C$_{21}$H$_{14}$BrN$_6$O (MH$^+$) 445.0412 found 445.0408.

The intermediate 5-bromo-2-[3,4-diaminophenyl] benzimidazole was prepared as follows.

a. 4-Bromo-o-phenylenediamine. 4-Bromo-2-nitroaniline 600 mg (2.76 mmol) was dissolved in 25 ml absolute ethanol and 2.72 g (14 mmol) SnCl$_2$ was added. The mixture was refluxed overnight. Ethanol was removed in vacuo and the mixture basified with 2N NaOH to pH 11. Ether extraction, drying the ether layer over anhydrous Na$_2$SO$_4$ and concentration in vacuo afforded 486 mg (2.6 mmol, 94% yield) of the crude 4-bromo-o-phenylenediamine which was used for the next step without characterization.

b. 5-Bromo-2-[3,4-nitrophenyl]benzimidazole. 4-Bromo-o-phenylenediamine (275 mg, 1.5 mmol) and 3,4-dinitrobenzaldehyde (300 mg, 1.5 mmol) in 2 ml nitrobenzene were heated at 145° C. overnight. The nitrobenzene was removed with a Kugelrohr. Column purification (1–10 % ethyl acetate/n-hexanes) afforded 209 mg (0.57 mmol, 39% yield) of the pure product; $^1$H NMR (DMSO+3 drops CF$_3$ COOH)δ 7.48 (dd,1H,J=1.82,8.76), 7.7 (d,1H,8.76), 7.96 (d,1H, 1.46), 8.45 (d,1H,8.5), 8.68 (dd,1H,J=1.84,8.5), 8.93 (d,1H,1.84); $^{13}$C NMR (DMSO+3 drops CF$_3$COOH) δ 116.36, 117.48, 118.66, 123.74, 127.05, 132.07, 134.49, 137.59, 140.23, 142.39, 142.81, 148.45.

c. 5-Bromo-2-[3,4-diaminophenyl]benzimidazole. 5-Bromo-2-[3,4-dinitrophenyl]benzimidazole (140 mg, 0.38 mmol) was dissolved in 8 ml absolute ethanol. 0.8 g SnCl$_2$ (4.2 mmol) was added and the mixture refluxed overnight. Ethanol was removed in vacuo and the mixture basified with 2N NaOH to pH 11. Repeated extraction with ether, drying the ether layer over anhydrous Na$_2$SO$_4$ and concentration in vacuo yielded (0.11 g, 0.37 mmol) of the crude diamine in 98% yield. The diamine was used without further purification; $^1$H NMR (DMSO-d$_6$) δ 6.63 (d,1H,J=8.1), 7.26 (m,2H), 7.39 (m,2H), 6.65 (d,1H,J=1.76).

The intermediate 5-formyl-2-hydroxybenzimidazole was prepared as follows.

d. 5-Cyano-2-hydroxybenzimidazole. 3,4-Diaminobenzonitrile (0.5 g, 3.8 mmol) and urea (0.25 g, 4.2 mmol) were heated together in 1 ml DMF at 145–150° C. for 9 h. The DMF was concentrated in vacuo and the mixture was suspended in water and extracted with ethyl acetate. Purification by column chromatography (elution with 60/40 ethyl acetate/n-hexanes) provided (0.53 g, 3.3 mmol) a yield of 89% of the product; IR (KBr) 3533, 3209, 2224, 1732, 1482, 1281; $^1$H NMR (DMSO-d$_6$+3 drops CF$_3$ COOH) δ 7.1 (d,1H,J=8.06), 7.09–7.41 (m,2H), 11.06 (s,1H), 11.19 (s,1H); $^{13}$C NMR (DMSO-d$_6$+3 drops CF$_3$COOH) δ 102.52,109.36, 111.61, 120.04, 126.03, 130.18, 133.93, 155.41.

e. 5-Formyl-2-hydroxybenzimidazole. 5-Cyano-2-hydroxybenzimidazole (0.5 g, 3.14 mmol) was mixed with Ni-Al catalyst (3 g), HCOOH (45 ml) and water (3 ml) and heated to reflux for 12 hrs. The hot mixture was filtered through a bed of celite and the filtrate concentrated in vacuo. pH of the mixture was adjusted to 9 with 2N NaOH and extraction was carried out with ethyl acetate. The ethyl acetate layer was dried over anhydrous Na$_2$SO$_4$ and concentrated in vacua. Column chromatographic purification, and elution with 65/35 ethyl acetate/n-hexanes provided 0.4 g (2.4 mmol, 76% yield) of the final compound; IR (KBr) 3261, 3160, 1677, 1631, 1477, 1282, 711; $^1$H NMR (DMSO-d$_6$+3 drops CF$_3$ COOH) δ 7.11 (d,1H,J=8.0), 7.41 (s,1H), 7.57 (dd,1H,J=1.54,8.0), 9.86 (s,1H), 10.99 (s,1H), 11.17 (s,1H); $^{13}$C NMR (DMSO-d$_6$+3 drops CF$_3$ COOH) δ 108.15, 108.67, 125.37, 130.1, 130.42, 135.64, 155.68, 191.99.

Example 12

5,6-Dibromo-2-[2'-(2"-trifluoromethylbenzimidazol-5"-yl]benzimidazol-5'yl]benzimidazole (22).

4,5-Dibromo-o-phenylenediamine (60 mg, 0.22 mmol) and 5-formyl-2-(2'-trifluoromethylbenzimidazol-5'-yl) benzimidazole (73 mg, 0.22 mmol) were heated in 10 ml nitrobenzene overnight at 150° C. The nitrobenzene was removed witha Kugelrohr and the mixture loaded on a column. Elution with 90/10 ethyl acetate/n-hexanes yielded 25 mg (20% yield, 0.05 mmol) of compound; mp>260° C.; $^1$H NMR (DMSO-d$_6$+3 drops CF$_3$COOH) δ 8.02–8.09 (m,2H), 8.14 (s,2H), 8.26–8.29 (m,2H), 8.57 (s,1H), 8.69 (s,1H).

The intermediate 5-formyl-2-(2'-trifluoromethylbenzimidazol-5'-yl)benzimidazole was prepared as follows.

a. 5-Cyano-2-(2'-trifluoromethylbenzimidazol-5'-yl) benzimidazole. 5-formyl-2-trifluoromethylbenzimidazole (1.5 g, 7 mmol) was mixed with 0.93 g of 3,4-diaminobenzonitrile (7 mmol) and 15 ml nitrobenzene. The mixture was heated overnight at 145° C. Nitrobenzene was removed with a Kugelrohr and the mixture was loaded onto a column. Elution with 40/60 ethyl acetate/n-hexanes gave 0.9 g (2.75 mmol) of the compound in 40% yield; mp>260° C.; IR (KBr) 3254, 2916, 2223, 1614, 1175; $^1$H NMR (DMSO-d$_6$+3 drops CF$_3$COOH) δ 7.74 (dd,1H,J=1.38, 8.4), 7.88 (d,1H,J=8.14), 7.98 (d,1H,J=8.78), 8.25–8.03 (m,2H), 8.63 (s,1H); $^{13}$C NMR (DMSO-d$_6$ +3 drops CF$_3$COOH) δ 105.62, 115.78, 116.35, 120.26, 123.06, 123.82, 127.18, 137.35, 139.65, 142.17, 142.96, 154.13.

b. 5-Formyl-2-(2'-trifluoromethylbenzimidazol-5'-yl) benzimidazole. 5-Cyano-2-(2'-trifluoromethylbenzimidlazol-5'-yl)benzimidazole (0.18 g, 0.54 mmol) was refluxed in 8 ml HCOOH with 2.5 ml water and 0.6 g Ni-Al catalyst for 7 hours at 110° C. The hot mixture was filtered through celite bed and the filtrate concentrated and its pH adjusted to 9.0 with 2N NaOH. Repeated extraction with ethyl acetate, drying the organic layer with anhydrous Na$_2$SO$_4$ and concentration in vacuo gave the crude product. Purification by column chromatography (elution with 1% methanol/ethyl acetate) yielded 87 mg (0.26 mmol, 49% yield) of the pure aldehyde; mp>260° C.; IR (KBr) 3411, 2966, 1679, 1310, 1153; $^1$H NMR (DMSO-d$_6$+3 drops CF$_3$COOH) δ 7.96–8.06 (m,3H), 8.30–8.32 (m,2H), 8.57 (s,1H), 10.15 (s,1H); $^{13}$C NMR (DMSO-d$_6$+3 drops CF$_3$COOH) δ 106.77, 112.51, 113.28, 117.79, 117.84, 118.28, 121.78, 123.96, 125.02, 132.98, 135.79, 139.62, 142.48, 153.51, 192.65.

The intermediate 4,5-dibromo-1,2-phenylenediamine was prepared as follows, using a modification of the procedures described in U.S. Pat. No. 4,264,600.

c. 3,4-Dibromoaniline. 3-Bromoaniline (3 g, 17.4 mmol) was dissolved in 15 ml $CH_2Cl_2$ and the reaction mixture was cooled to −10° C. in an ice-salt bath. 2,4,4,6-Tetrabromo-2,5-cyclohexadienone, (9.29 g, 0.02 mmol) was added in small portions with constant stirring. The reaction mixture was stirred for a period of 7 hours at 0° C. after which the reaction was quenched with 2N NaOH (10 ml). The aqueous layer was extracted with $CH_2Cl_2$ and the organic layer was dried over anhydrous $Na_2SO_4$. The $CH_2Cl_2$ layer was concentrated in vacuo and purified by column chromatography. Elution with 0–3% ethyl acetate/n-hexanes yielded 3.2 g (12.7 mmol, 73%) of pure product; mp 80–81° C.; IR (KBr) 3406, 3318, 3210, 1583, 1464, 1287, 1108, 860, 668; $^1H$ NMR ($CDCl_3$) δ 6.49 (dd, 1H,J=2.7,8.6), 6.7 (d,1H,J=2.64), 7.32 (d,1H,J=8.6); $^{13}C$ NMR($CDCl_3$) δ 112.6, 116, 120.1, 125.45, 134.26, 147.08.

d. 3,4-Dibromoacetanilide. 3,4-Dibromoaniline (3.2 g, 12.7 mmol) was mixed with 13 ml acetic anhydride and heated at 110° C. for 2 hours after which it was poured over ice cold water. The aqueous layer was extracted with ethyl acetate, 0.1N HCl and 1N NaOH, and the organic layer was dried over anhydrous $Na_2SO_4$. The organic layer was concentrated in vacuo and purified by column chromatography. Elution with 1–50% ethyl acetate/n-hexanes yielded 2.6 g (9 mmol, 71% yield) of the acetanilide: mp 91–93° C.; IR (KBr) 3293, 3172, 1668, 1589,1552, 1522, 1373, 813; $^1H$ NMR ($CDCl_3$) δ 2.17(s,3H), 7.33 (dd,1H,J=2.4,8.66), 7.52 (d,1H,J= 8.68), 7.87 (d,1H, J=2.4); $^{13}C$ NMR ($CDCl_3$) δ 25.07, 119.64, 120.35, 125.04, 125.38, 134.13, 138.40, 168.96.

e. 3,4-Dibromo-6-nitroacetanilide. 3,4-Dibromoacetanilide (2.64 g, 9 mmol) was dissolved in 8 ml conc. $H_2SO_4$ (chilled in ice-salt bath) at a temperature of 0° C. To this solution was added 1 ml chilled nitrating mixture (equal volumes of conc. $H_2SO_4$ and fuming $HNO_3$) and the mixture stirred for 20 min. The reaction mixture was poured into ice water and neutralized with ammonium hydroxide to pH of 9.0. The yellow precipitate was filtered and purified by column chromatography. Elution with 1–4% ethyl acetate/n-hexanes yielded 2.1 g (6.15 mmol, 68%) of the 3,4-dibromo-6-nitroacetanilide: mp 141–142° C.; IR (KBr) 3340, 3128, 1693, 1569, 1479, 1332, 1268; $^1H$ NMR ($CDCl_3$) δ 2.3 (s,3H), 8.46 (s, 1H), 9.22 (s,1 H); $^{13}C$ NMR ($CDCl_3$) δ 26.14, 118.67, 126.86, 130.86, 134.51, 134.59, 136.98, 169.40.

f. 3,4-Dibromo-6-nitroaniline. 3,4-Dibromo-6-nitroacetanilide (2.1 g, 6.15 mmol) was heated to refluxing temperature for 2 hours with 40 ml of 6N HCl. The reaction mixture was then poured over an ice-water mixture and stirred. The pH of the solution was adjusted to 9.0 with NaOH. The resulting bright yellow precipitate was filtered, washed with cold water and dried to yield (1.78 g, 6 mmol, 98%) of pure product; mp 204–205° C.; IR (KBr) 3475, 3355, 3097, 1612, 1478, 1241, 1122, 914; $^1H$ NMR ($CDCl_3$) δ 6.05 (brs,2H), 7.18 (s,1H), 8.37 (s,1H); $^{13}C$ NMR ($CDCl_3$) δ 111.23, 123.22, 129.34, 130.59, 133.61, 142.36.

g. 4,5-Dibromo-1,2-phenylenediamine. 3,4-Dibromo-6-nitroaniline (189 mg, 0.64 mmol) was dissolved in 8 ml anhydrous ethanol to which was added about 400 mg Raney Nickel. The hydrogenation apparatus was at a hydrogen pressure 50 psi. After 45 min. the deep yellow color originally present was completely discharged indicating complete reduction of the nitro to the amine groups. The reaction mixture was filtered through celite and the bed was washed with methanol. The methanol was concentrated in vacuo to give 135 mg of the crude diamine in 82% yield. The crude diamine was used as such without further purification; $^1H$ NMR ($CDCl_3$) δ 3.37 (br,4H), 6.93 (s,2H); $^{13}C$ NMR ($CDCl_3$) δ 113.98, 120.95, 135.84.

Example 13

5-Phenyl-6methoxy-2-[2'(benzimidazol-5"-yl) benzimidazol-5'-yl]benzimidazole (15).

4-Methoxy-5-phenyl-1,2 phenylenediamine (139 mg, 0.65 mmol) and 5-formyl-2-(benzimidazol-5'-yl) benzimidazole (170 mg, 0.65 mmol) were heated together in nitrobenzene (5 ml) overnight at 145° C. Nitrobenzene was removed with a Kugelrohr and the compound was loaded onto a column. (1–10%) methanol/ethyl acetate gave 120 mg (41%) of pure product; mp>280° C.; IR (KBr) 3298, 3050, 2987, 1630, 1541, 1438, 1283; $^1H$ NMR (DMSO-$d_6$+3 drops $CF_3COOH$) δ 3.92 (s,3H), 7.39–7.57 (m,6H), 7.72 (s,1H), 8.11–8.15 (m,1H), 8.19–8.27 (m,2H), 8.47 (dd,1H,J=1.46,8.07), 8.64 (s,1H), 8.76 (s,1H), 9.75 (s,1H); $^{13}C$ NMR (DMSO-$d_6$+3 drops $CF_3COOH$) δ 56.40, 95.73, 114.62, 115.18, 116.02, 116.15, 119.03, 119.07, 125.59, 126.29, 127.63, 127.67, 128.34, 129.79, 130.69, 131.54, 132.42, 133.38, 137.59, 148.81, 152.84, 156.82; HRMS (FAB) calculated for $C_{28}H_{21}N_6O$ ($MH^+$) 457.1777, found 457.1770.

The intermediate 4-methoxy-5-phenyl-1,2 phenylenediamine was prepared as follows.

a. 4-Methoxy-2-nitro5-phenylaniline. 3-Bromo4-methoxy-6-nitroaniline (400 mg, 1.62 mmol) was dissolved in DME (20 ml). Tetrakispalladium triphenyl phosphine (94 mg, 0.08 mmol) served as the catalyst. To this mixture was added phenyl boronic acid(300 mg, 1.01 mmol) and 2M $Na_2CO_3$ (1.8 ml) and the mixture refluxed at 90° C. overnight. The reaction mixture was concentrated in vacuo and purified by flash column chromatography. (1–10%) ethyl acetate/n-hexanes gave 280 mg (1.14 mmol) of pure product in 71% yield; IR (KBr) 3435, 3328, 2933, 1570, 1480, 1227, 1029, 692; $^1H$ NMR ($CDCl_3$) δ 3.80 (s,3H), 5.94 (br,2H), 6.79 (s,1H), 7.39–7.64 (m,5H), 7.64 (s,1H); $^{13}C$ NMR ($CDCl_3$) δ 56.63, 106.76, 121.26, 128.69, 128.72, 128.76, 128.79, 128.92, 129.71, 136.69, 140.24, 141.42, 148.65; MS (FAB) calculated for $C_{13}H_{12}N_2O_3$ 244.0848, found 244.0847.

b. 4-Methoxy-5-phenyl-1,2 phenylenediamine. 4-Methoxy-2-nitro-5-phenyl-aniline (165 mg, 0.68 mmol) in ethyl acetate (20 ml) was reduced using 20 mg of 10% Pd/C as the catalyst, overnight. The mixture was filtered through celite bed and the bed was washed with methanol. All the washings were concentrated in vacuo to yield 139 mg (96% yield) of the crude diamine which was used without further purification; $^1H$ NMR ($CDCl_3$) δ 3.49 (brs,4H), 3.71 (s,3H), 6.42 (s, 1H), 6.74 (s,1H), 7.26–7.52 (m,5H); $^{13}C$ NMR ($CDCl_3$) δ 56.81, 101.77, 120.93, 127.53, 128.39, 128.45, 128.49, 129.82, 129.96, 136.64, 139.17, 142.37, 153.73.

The intermediate 3-bromo-4-methoxy-6-nitro-aniline used in sub-part a is commercially available (Aldrich Chemical Company).

The intermediate 5-fornyl-2-(benzimidazol-5'-yl) benzimidazole was prepared as described by Sun et al. *J. Med. Chem.* 1995, 38, 3638–3644.

Example 14

5,6-Diphenyl-2-[2'(benzimidazol-5"-yl)benzimidazol-5'-yl]benzimidazole (16).

4,5-Diphenyl-1,2-phenylenediamine (151 mg, 0.58 mmol) and 5-formyl-2-(benzimidazol-5'-yl)benzimidazole (152 mg, 0.58 mmol) were heated in nitrobenzene (4 ml) overnight at 145° C. under nitrogen. The nitrobenzene was removed with a Kugelrohr. Compound was purified by flash column chromatography. Elution with (2–10%) methanol/ethyl acetate gave 108 mg (0.22 mmol) of pure yellow compound in 37% yield. mp>280° C.; IR (KBr) 3399, 3059, 1629, 1551, 1441, 1292; $^1$H NMR (DMSO-$d_6$ +3 drops $CF_3COOH$) δ 7.17–7.33 (m,10H), 7.84 (s,2H), 8.06–8.25 (m,3H), 8.49 (dd,1H,J=1.18,8.89), 8.66 (s,1H), 8.75 (s,1H), 9.69 (s,1H); $^{13}$C NMR (DMSO-$d_6$+3 drops $CF_3COOH$) δ 113.94, 115.24, 115.84, 116.15, 116.32, 117.89, 123.34, 126.32, 126.66, 127.86, 128.38, 128.42, 128.46, 130.05, 131.77, 131.89, 133.03, 138.87, 138.97, 140.62, 141.19, 160.97, 153.71; HRMS (FAB) calculated for $C_{33}H_{23}N_6$ (MH$^+$) 503.1984 found 503.1989.

The intermediate 4,5-diphenyl-1,2-phenylenediamine was prepared as follows.

a. 4,5-Diphenyl-2-nitroaniline. 3,4-Dibromo-6-nitroaniline (332 mg, 1.12 mmol) was dissolved in DME (20 ml). Tetrakis(triphenylphosphine)palladium (65 mg, 0.06 mmol), phenyl boronic acid (200 mg, 1.64 mmol), and 2M $Na_2CO_3$ (10 ml) were added to the reaction mixture and refluxed at 90° C. overnight. The reaction mixture was concentrated in vacuo and loaded onto a column. (1–3%) ethyl acetate/n-hexanes afforded 259 mg of pure yellow compound in 80% yield; mp 139–141° C.; IR (KBr) 3476, 3363, 2924, 1621, 1476, 1263, 1089; $^1$H NMR (CDCl$_3$) δ 6.11 (brs,2H), 6.86 (s,1H), 7.04–7.09 (m,5H), 7.15–7.26 (m,5H), 8.21 (s,1H); $^{13}$C NMR (CDCl$_3$) δ 120.56, 127.22, 127.66, 128.20, 128.26, 128.52, 128.53, 129.31, 129.39, 129.47, 129.77, 130.14, 130.93, 131.79, 139.85, 139.94, 144.08, 149.03.

b. 4,5-Diphenyl-1,2-phenylenediamine. 4,5-Diphenyl-2-nitroaniline (200 mg, 0.69 mmol) in ethanol (50 ml) was reduced using 40 mg 10% Pd/C. Hydrogenation was carried out at 40 psi pressure for 10 hours. The mixture was filtered through celite and the bed washed with methanol. The methanol layer was concentrated in vacuo to yield 151 mg of the crude diamine in 84% yield. The crude diamine was used as such without purification. $^1$H NMR (CD$_3$OD) δ 6.78 (s,2H), 7.01–7.16 (m,10H); $^{13}$C NMR (CD$_3$OD) δ 118.08, 121.23, 127.17, 127.66, 130.44, 131.76, 138.32.

Example 15

5,6-Dibromo-2-[2'-(benzimidazol-5"-yl)benzimidazol-5'-yl] benzimidazole (20).

4,5-Dibromo-1,2-phenylenediamine (128 mg, 0.48 mmol) and 5-formyl-2-(benzimidazol-5'-yl)benzimidazole (126 mg, 0.48 mmol) were heated in nitrobenzene (6 ml) at 145° C. overnight. The nitrobenzene was removed with a Kugelrohr and the mixture loaded on a column for purification. Elution with (1–10%) methanol/ethyl acetate gave 0.1 gm (41%) of pure compouind; mp>260° C.; IR(KBr) 3405, 3198, 1626, 1544, 1385, 1292; $^1$H NMR (DMSO-$d_6$+3 drops $CF_3COOH$) δ 8.03–8.13 (m,2H), 8.17 (s,2H), 8.25 (d,1H,J=9.16), 8.42 (d,1H,J=8.64), 8.59 (s,1H), 8.74 (s,1H), 9.75 (s,1H); $^{13}$C NMR (DMSO-$d_6$+3 drops $CF_3COOH$) δ 114.73, 114.96, 115.77, 115.99, 118.93, 119.61, 120.73, 123.29, 124.47, 125.56, 131.49, 133.47, 134.77, 135.79, 137.95, 151.93, 152.31; HRMS (FAB) calculated for $C_{21}H_{13}Br_2N_6$ (MH$^+$) 506.9568 found 506.9574.

The intermediate 4,5-dibromo-1,2-phenylenediamine was prepared as described at Example 12c-g.

Example 16

5-Bromo-6-metboxy-2-[2'-(benzimidazol-5"-yl)benzimidazol-5'yl]benzimidazole (21)

In nitrobenzene (4ml), 4-bromo-5-methoxy-1,2-phenylenediamine (123 mg, 0.57 mmol) and 5-formyl-2-(benzimidazol-5'-yl)benzimidazole (150 mg, 0.57 mmol) were heated at 145° C. overnight under nitrogen. Nitrobenzene was removed with a Kugelrohr. Chromatographic separation with (1–10%) methanol/ethyl acetate afforded 104 mg (40%) of pure compound; mp >280° C.; $^1$H NMR (DMSO-$d_6$+3 drops $CF_3COOH$) δ 3.91 (s,3H), 7.17–7.29 (m,1H), 7.78 (d,1H,J=8.84), 8.00–8.13 (m,3H), 8.49–8.53 (m,1H), 8.66 (s,1H), 8.79 (s,1H), 9.69 (s,1H); $^{13}$C NMR (DMSO-$d_6$+3 drops $CF_3COOH$) δ 56.16, 96.43, 114.06, 114.97, 115.55, 115.79, 115.89, 116.35, 117.97, 118.42, 123.11, 125.30, 125.58, 126.33, 127.43, 131.85, 133.05, 133.11, 138.39, 140.84, 149.04, 153.44; HRMS (FAB) calculated for $C_{22}H_{16}BrN_6O$ (MH$^+$)

The intermediate 4-bromo-5-methoxy-1,2-phenylenediamine was prepared as follows.

a. 4-Bromo-5-methoxy-1,2-phenylenediamine. 3-Bromo-4-methoxy-6-nitroaniline (150 mg, 0.61 mmol) (Aldrich Chemical Company) was dissolved in ethanol (10 ml) and hydrogenation was carried out using 350 mg Raney Nickel for 30 min. The reaction mixture was filtered through celite bed and washed with methanol. The methanolic layer was dried in vacuo to give 127 mg of the crude diamnine in 97.40% yield, which was used as such withoult purification; $^1$H NMR (CDCl$_3$) δ 3.20 (brs,2H), 3.39 (brs,2H), 3.8 (s,3H), 8.36 (s,1H), 6.89 (s,1H); $^{13}$C NMR (CDCl$_3$) δ 57.35, 100.38, 102.27, 122.52, 128.69, 136.68, 150.94.

Example 17

The following illustrate representative pharmaceutical dosage forms, containing a compound of formula I ('Compound X'), for therapeutic or prophylactic use in humans.

| (i) Tablet 1 | mg/tablet |
|---|---|
| 'Compound X' | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| 'Compound X' | 20.0 |
| Microcrystalline cellulose | 410.0 |
| Starch | 50.0 |
| Sodium starch glycolate | 15.0 |
| Magnesium stearate | 5.0 |
| | 500.0 |

-continued

| (iii) Capsule | mg/capsule |
|---|---|
| 'Compound X' | 10.0 |
| Colloidal silicon dioxide | 1.5 |
| Lactose | 465.5 |
| Pregelatinized starch | 120.0 |
| Magnesium stearate | 3.0 |
|  | 600.0 |

| (iv) Injection 1 (1 mg/ml) | mg/ml |
|---|---|
| 'Compound X' (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0–7.5) | q.s. |
| Water for injection | q.s. ad 1 mL |

| (v) Injection 2 (10 mg/ml) | mg/ml |
|---|---|
| 'Compound X' (free acid form) | 10.0 |
| Monobasic sodium phosphate | 0.3 |
| Dibasic sodium phosphate | 1.1 |
| Polyethylene glycol 400 | 200.0 |
| 01N Sodium hydroxide solution (pH adjustment to 7.0–7.5) | q.s. |
| Water for injection | q.s. ad 1 mL |

| (vi) Aerosol | mg/can |
|---|---|
| 'Compound X' | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A compound of formula I:

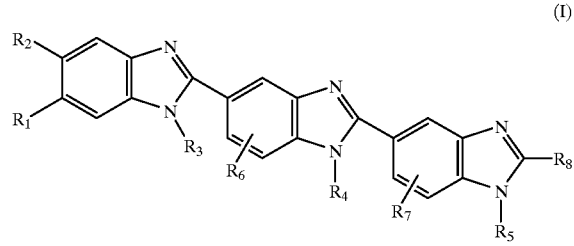

(I)

wherein $R_1$ and $R_2$ are each independently hydrogen, $(C_1-C_6)$alkyl, $(C_3-C_6)$cycloalkyl, $(C_3-C_6)$cycloalkyl$(C_1-C_6)$alkyl, $(C_1-C_6)$alkoxy, $(C_3-C_6)$cycloalkyl$(C_1-C_6)$alkoxy, hydroxy, halo, nitro, cyano, mercapto, carboxy, hydroxy$(C_1-C_6)$alkyl, halo$(C_1-C_6)$alkyl, trifluoromethoxy, $(C_1-C_6)$alkanoyl, $(C_1-C_6)$alkoxycarbonyl, $(C_1-C_6)$alkylthio, $(C_1-C_6)$alkanoyloxy, aryl, heteroaryl, aryl$(C_1-C_6)$alkyl, or heteroaryl$(C_1-C_6)$alkyl; or $R_1$ and $R_2$ taken together are methylenedioxy; or $R_1$ and $R_2$ taken together are benzo;

$R_3$, $R_4$, and $R_5$ are each independently selected from the group consisting of hydrogen, $(C_1-C_6)$alkyl, $(C_3-C_6)$cycloalkyl, $(C_1-C_6)$alkanoyl, $(C_1-C_6)$alkoxycarbonyl, $(C_2-C_6)$alkanoyloxy, aryl, heteroaryl, aryl$(C_1-C_6)$alkyl, and heteroaryl$(C_1-C_6)$alkyl;

$R_6$ and $R_7$ are each independently hydrogen, $(C_1-C_6)$alkyl, $(C_3-C_6)$cycloalkyl, $(C_3-C_6)$cycloalkyl$(C_1-C_6)$alkyl, $(C_1-C_6)$alkoxy, $(C_3-C_6)$ycloalkyl$(C_1-C_6)$alkoxy, hydroxy, halo, nitro, cyano, mercapto, carboxy, hydroxy$(C_1-C_6)$alkyl, halo$(C_1-C_6)$alkyl, trifluoromethoxy, $(C_1-C_6)$alkanoyl, $(C_1-C_6)$alkoxycarbonyl, $(C_1-C_6)$alkylthio, or $(C_1-C_6)$alkanoyloxy;

$R_8$ is hydroxy, halo, nitro, cyano, mercapto, carboxy, $(C_1-C_6)$alkoxy, $(C_3-C_6)$cycloalkyl$(C_1-C_6)$alkoxy, —$NR_aR_b$, halo$(C_1-C_6)$alkyl, trifluoromethoxy, $(C_1-C_6)$alkanoyl, $(C_1-C_6)$alkoxycarbonyl, $(C_1-C_6)$alkylthio, $(C_1-C_6)$alkanoyloxy, aryloxy, or heteroaryloxy; or $R_8$ is $(C_1-C_6)$alkyl substituted by 1, 2, or 3 substituents independently selected from the group consisting of hydroxy, nitro, cyano, mercapto, carboxy, $(C_1-C_6)$alkoxy, $(C_3-C_6)$cycloalkyl$(C_1-C_6)$alkoxy, —$NR_aR_b$, trifluoromethoxy, $(C_1-C_6)$alkanoyl, $(C_1-C_6)$alkoxycarbonyl, $(C_1-C_6)$alkylthio, $(C_1-C_6)$alkanoyloxy, aryloxy, and heteroaryloxy; and each $R_a$ and $R_b$ is independently hydrogen, $(C_1-C_6)$alkyl, $(C_1-C_6)$alkanoyl, $(C_1-C_6)$alkoxycarbonyl, aryl, heteroaryl, aryl$(C_1-C_6)$alkyl, heteroaryl$(C_1-C_6)$alkyl, arylcarbonyl, or heteroarylcarbonyl; or $R_a$ and $R_b$ together with the nitrogen to which they are attached are pyrrolidino, piperidino, or morpholino.

wherein any aryl, heteroaryl, or benzo of $R_1$-$R_5$, $R_8$, $R_a$, and $R_b$ may optionally be substituted by 1, 2, or 3 substituents independently selected from the group consisting of $(C_1-C_6)$alkyl, $(C_3-C_6)$cycloalkyl, $(C_3-C_6)$cycloalkyl$(C_1-C_6)$alkyl, $(C_1-C_6)$alkoxy, $(C_3-C_6)$cycloalkyl$(C_1-C_6)$alkoxy, hydroxy, halo, nitro, cyano, mercapto, carboxy, hydroxy$(C_1-C_6)$alkyl, halo$(C_1-C_6)$alkyl, trifluoromethoxy, $(C_1-C_6)$alkanoyl, $(C_1-C_6)$alkoxycarbonyl, $(C_1-C_6)$alkylthio, and $(C_1-C_6)$alkanoyloxy;

or a pharmaceutically acceptable salt thereof.

2. The compound of claim 1 wherein $R_2$ is phenyl, optionally substituted by 1, 2, or 3 substituents independently selected from the group consisting of $(C_1-C_6)$alkyl, $(C_1-C_6)$alkoxy, hydroxy, halo, nitro, cyano, mercapto, carboxy, halo$(C_1-C_6)$alkyl, trifluoromethoxy, $(C_1-C_6)$alkanoyl, $(C_1-C_6)$alkoxycarbonyl, $(C_1-C_6)$alkylthio, and $(C_1-C_6)$alkanoyloxy.

3. The compound of claim 1 wherein $R_2$ is phenyl.

4. The compound of claim 1 wherein $R_1$ is hydrogen.

5. The compound of claim 1 wherein $R_1$ is halo.

6. The compound of claim 1 wherein $R_1$ and $R_2$ are each halo.

7. The compound of claim 1 wherein $R_1$ and $R_2$ are each bromo.

8. The compound of claim 1 wherein $R_3$, $R_4$, and $R_5$ are each hydrogen.

9. The compound of claim 1 wherein $R_6$ and $R_7$ are each hydrogen.

10. The compound of claim 1 wherein $R_6$ is $(C_1-C_6)$alkoxy, hydroxy, halo, nitro, cyano, mercapto, carboxy, hydroxy$(C_1-C_6)$alkyl, halo$(C_1-C_6)$alkyl, trifluoromethoxy, $(C_1-C_6)$alkanoyl, $(C_1-C_6)$alkoxycarbonyl, $(C_1-C_6)$alkylthio, or $(C_1-C_6)$alkanoyloxy.

11. The compound of claim 1 wherein $R_7$ is $(C_1-C_6)$alkoxy, hydroxy, halo, nitro, cyano, mercapto, carboxy, hydroxy($C_1$-$C_6$)alkyl, halo($C_1$-$C_6$)alkyl, trifluoromethoxy, ($C_1$-$C_6$)alkanoyl, ($C_1$-$C_6$)alkoxycarbonyl, ($C_1$-$C_6$)alkylthio, or ($C_1$-$C_6$)alkanoyloxy.

12. The compound of claim 1 wherein $R_8$ is hydroxy, halo, nitro, cyano, mercapto, carboxy, ($C_1$-$C_6$)alkoxy, —$NR_aR_b$, halo($C_1$-$C_6$)alkyl, trifluoromethoxy, ($C_1$-$C_6$)alkanoyl, ($C_1$-$C_6$)alkoxycarbonyl, ($C_1$-$C_6$)alkylthio, or ($C_1$-$C_6$)alkanoyloxy.

13. The compound of claim 1 wherein $R_8$ is ($C_1$-$C_6$)alkyl substituted by 1, 2, or 3 hydroxy, nitro, cyano, mercapto, carboxy, ($C_1$-$C_6$)alkoxy, —$NR_aR_b$, trifluoromethoxy, ($C_1$-$C_6$)alkanoyl, ($C_1$-$C_6$)alkoxycarbonyl, ($C_1$-$C_6$)alkylthio, or ($C_1$-$C_6$)alkanoyloxy.

14. The compound of claim 1 wherein $R_8$ is ($C_1$-$C_6$)alkyl substituted by hydroxy, nitro, cyano, mercapto, carboxy, ($C_1$-$C_6$)alkoxy, —$NR_aR_b$, trifluoromethoxy, ($C_1$-$C_6$)alkanoyl, ($C_1$-$C_6$)alkoxycarbonyl, ($C_1$-$C_6$)alkylthio, or ($C_1$-$C_6$)alkanoyloxy.

15. The compound of claim 1 wherein $R_8$ is halo or trifluoromethyl.

16. The compound of claim 1 wherein $R_8$ is trifluoromethyl.

17. A pharmaceutical composition comprising a compound of claim 1, in combination with a pharmaceutically acceptable carrier.

18. A compound of formula I:

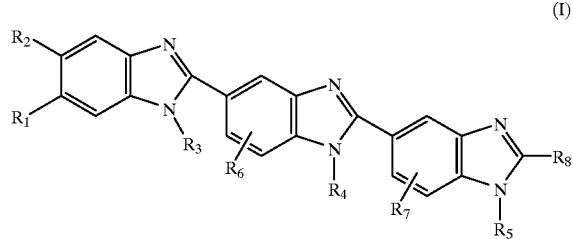

(I)

wherein $R_1$ and $R_2$ are each independently ($C_1$-$C_6$)alkyl, ($C_3$-$C_6$)cycloalkyl, ($C_3$-$C_6$)cycloalkyl($C_1$-$C_6$)alkyl, ($C_1$-$C_6$)alkoxy, ($C_3$-$C_6$)cycloalkyl($C_1$-$C_6$)alkoxy, hydroxy, halo, nitro, cyano, mercapto, carboxy, hydroxy($C_1$-$C_6$)alkyl, halo($C_1$-$C_6$)alkyl, trifluoromethoxy, ($C_1$-$C_6$)alkanoyl, ($C_1$-$C_6$)alkoxycarbonyl, ($C_1$-$C_6$)alkylthio, ($C_1$-$C_6$)alkanoyloxy, aryl, heteroaryl, aryl($C_1$-$C_6$)alkyl, or heteroaryl($C_1$-$C_6$)alkyl; or $R_1$ and $R_2$ taken together are methylenedioxy;

$R_3$, $R_4$, and $R_8$ are each independently selected from the group consisting of hydrogen, ($C_1$-$C_6$)alkyl, ($C_3$-$C_6$)cycloalkyl, ($C_1$-$C_6$)alkanoyl, ($C_1$-$C_6$)alkoxycarbonyl, ($C_2$-$C_6$)alkanoyloxy, aryl, heteroaryl, aryl($C_1$-$C_6$)alkyl, and heteroaryl($C_1$-$C_6$)alkyl;

$R_6$ and $R_7$ are each independently hydrogen, ($C_1$-$C_6$)alkyl, ($C_3$-$C_6$)cycloalkyl, ($C_3$-$C_6$)cycloalkyl($C_1$-$C_6$)alkyl, ($C_1$-$C_6$)alkoxy, ($C_3$-$C_6$)cycloalkyl($C_1$-$C_6$)alkoxy, hydroxy, halo, nitro, cyano, mercapto, carboxy, hydroxy($C_1$-$C_6$)alkyl, halo($C_1$-$C_6$)alkyl, trifluoromethoxy, ($C_1$-$C_6$)alkanoyl, ($C_1$-$C_6$)alkoxycarbonyl, ($C_1$-$C_6$)alkylthio, or ($C_{1-6}$)alkanoyloxy; and $R_8$ is hydrogen, ($C_1$-$C_6$)alkyl, aryl, or heteroaryl;

wherein any aryl or heteroaryl of $R_1$-$R_5$ and $R_8$ may optionally be substituted by 1, 2, or 3 substituents independently selected from the group consisting of ($C_1$-$C_6$)alkyl, ($C_3$-$C_6$)cycloalkyl, ($C_3$-$C_6$)cycloalkyl ($C_1$-$C_6$)alkyl, ($C_1$-$C_6$)alkoxy, ($C_3$-$C_6$)cycloalkyl($C_1$-$C_6$)alkoxy, hydroxy, halo, nitro, cyano, mercapto, carboxy, hydroxy($C_1$-$C_6$)alkyl, halo($C_1$-$C_6$)alkyl, trifluoromethoxy, ($C_1$-$C_6$)alkanoyl, ($C_1$-$C_6$)alkoxycarbonyl, ($C_1$-$C_6$)alkylthio, and ($C_1$-$C_6$)alkanoyloxy; or a pharmaceutically acceptable salt thereof.

19. The compound of claim 18 wherein $R_1$ and $R_2$ are each independently ($C_1$-$C_6$)alkoxy, hydroxy, halo, nitro, cyano, mercapto, carboxy, hydroxy($C_1$-$C_6$)alkyl, halo($C_1$-$C_6$)alkyl, trifluoromethoxy, or aryl.

20. The compound of claim 18 wherein $R_1$ and $R_2$ taken together are methylenedioxy.

21. The compound of claim 18 wherein $R_1$ and $R_2$ are each halo.

22. The compound of claim 18 wherein $R_1$ and $R_2$ are each bromo.

23. The compound of claim 18 wherein $R_1$ and $R_2$ are each independently phenyl or methoxy.

24. The compound of claim 18 wherein $R_3$, $R_4$, and $R_5$ are each hydrogen.

25. The compound of claim 18 wherein $R_6$ is ($C_1$-$C_6$)alkoxy, hydroxy, halo, nitro, cyano, mercapto, carboxy, hydroxy($C_1$-$C_6$)alkyl, halo($C_1$-$C_6$)alkyl, trifluoromethoxy, ($C_1$-$C_6$)alkanoyl, ($C_1$-$C_6$)alkoxycarbonyl, ($C_1$-$C_6$)alkylthio, or ($C_1$-$C_6$)alkanoyloxy.

26. The compound of claim 18 wherein $R_7$ is ($C_1$-$C_6$)alkoxy, hydroxy, halo, nitro, cyano, mercapto, carboxy, hydroxy($C_1$-$C_6$)alkyl, halo($C_1$-$C_6$)alkyl, trifluoromethoxy, ($C_1$-$C_6$)alkanoyl, ($C_1$-$C_6$)alkoxycarbonyl, ($C_1$-$C_6$)alkylthio, or ($C_1$-$C_6$)alkanoyloxy.

27. The compound of claim 18 wherein $R_8$ is hydrogen.

28. The compound of claim 18 wherein $R_8$ is ($C_1$-$C_6$)alkyl.

29. The compound of claim 18 wherein $R_8$ is aryl, optionally substituted by 1, 2, or 3 substituents independently selected from the group consisting of ($C_3$-$C_6$)cycloalkyl, ($C_3$-$C_6$)cycloalkyl($C_1$-$C_6$)alkyl, ($C_3$-$C_6$)cycloalkyl($C_1$-$C_6$) alkoxy, hydroxy, halo, nitro, cyano, mercapto, carboxy, hydroxy($C_1$-$C_6$)alkyl, halo($C_1$-$C_6$)alkyl, trifluoromethoxy, ($C_1$-$C_6$)alkanoyl, ($C_1$-$C_6$)alkoxycarbonyl, ($C_1$-$C_6$)alkylthio, and ($C_1$-$C_6$)alkanoyloxy.

30. The compound of claim 18 wherein $R_8$ is heteroaryl, optionally substituted by 1, 2, or 3 substituents independently selected from the group consisting of ($C_1$-$C_6$)alkyl, ($C_3$-$C_6$)cycloalkyl, ($C_3$-$C_6$)cycloalkyl($C_1$-$C_6$)alkyl, ($C_1$-$C_6$)alkoxy, ($C_3$-$C_6$)cycloalkyl($C_1$-$C_6$)alkoxy, hydroxy, halo, nitro, cyano, mercapto, carboxy, hydroxy($C_1$-$C_6$)alkyl, halo ($C_1$-$C_6$)alkyl, trifluoromethoxy, ($C_1$-$C_6$)alkanoyl, ($C_1$-$C_6$) alkoxycarbonyl, ($C_1$-$C_6$)alkylthio, and ($C_1$-$C_6$)alkanoyloxy.

31. A pharmaceutical composition comprising a compound of claim 18, in combination with a pharmaceutically acceptable carrier.

* * * * *

UNITED STATES PATENT AND TRADEMARK OFFICE
CERTIFICATE OF CORRECTION

PATENT NO. : 6,399,642 B2
DATED : June 4, 2002
INVENTOR(S) : Edmond J. LaVoie et al.

It is certified that error appears in the above-identified patent and that said Letters Patent is hereby corrected as shown below:

Title page,
Item [56], OTHER PUBLICATIONS, delete "imtermediates" and insert -- intermediates --, therefor.
Delete "Cherif, A.,   et   al.,  " and insert -- Cherif, A., et al., --, therefor.

Column 26,
Line 8, delete "$(C_3-C_6)$ycloalkyl" and insert -- $(C_3-C_6)$cycloalkyl --, therefor.

Column 27,
Line 50, delete "$R_8$" and insert -- $R_5$ --, therefor.
Line 61, delete "$(C_{1-6})$" insert -- $(C_1-C_6)$ --, therefor.

Column 28,
Line 42, delete "$R_8$is" and insert -- $R_8$ is --, therefor.

Signed and Sealed this

Twenty-ninth Day of April, 2003

JAMES E. ROGAN
*Director of the United States Patent and Trademark Office*